United States Patent [19]
Carbonetti et al.

[11] Patent Number: 6,068,992
[45] Date of Patent: May 30, 2000

[54] PRODUCTION OF GONORRHEAL PI PROTEINS AND VACCINES

[75] Inventors: Nicholas H. Carbonetti; P. Frederick Sparling, both of Chapel Hill, N.C.

[73] Assignee: The University of North Carolina at Chapel Hill, Chapel Hill, N.C.

[21] Appl. No.: 08/965,085

[22] Filed: Nov. 6, 1997

Related U.S. Application Data

[63] Continuation of application No. 07/983,995, Dec. 1, 1992, Pat. No. 5,736,361, which is a continuation of application No. 07/689,663, Apr. 23, 1991, abandoned, which is a continuation of application No. 07/242,758, Sep. 9, 1988, abandoned, which is a continuation-in-part of application No. 07/124,727, Nov. 24, 1987, abandoned.

[51] Int. Cl.[7] .......................... C12P 21/02; C12N 15/31; C12N 1/21; C12N 15/70
[52] U.S. Cl. ................ 435/69.3; 435/320.1; 435/252.3; 435/252.33; 435/256.11; 536/23.7
[58] Field of Search .......................... 536/23.7; 435/69.3, 435/320.1, 252.3, 252.33, 256.11, 325.1

[56] References Cited

U.S. PATENT DOCUMENTS 5,736,361  4/1998  Carbonetti et al. .................... 435/69.3

OTHER PUBLICATIONS

Gotschlich et al (PNAS 84:8135–8139), 1987.
Ganss, M.T. et al. In: The Pathogenic Neisseriae, ed. G.K. Schoolnick, Amer. Soc. Microbiol., pp. 259–264, 130–131, 1985.
Danielsson et al (Infection and Immunity 52(2):529–533), 1986.

*Primary Examiner*—Mary E. Mosher
*Attorney, Agent, or Firm*—Hoffmann & Baron, LLP; Irving N. Feit

[57] ABSTRACT

The present invention relates to a gene sequence coding for Protein I of *Neisseria gonorrhoeae*, and cloning vector and host organisms containing same. Also disclosed are oligonucleotides useful as diagnostic probes for the detection of *N. gonorrhoeae* infection.

12 Claims, 11 Drawing Sheets

```
           1     2    3    4    5    6    7    8    9   10   11   12 protein   Asp - Val - Thr - Leu - Tyr - Gly - Ala - Ile - Lys - Ala - Gly - Val mRNA  5' GAU  GUU  ACU  CUU  UAU  GGU  GCU  AUU  AAA  GCU  GGU  GU 3'
                    C    C    C         C    C         C    C
                    A    A    A         A    A    G    A    A
                    G    G    G         G    G         G    G oligo NC1 ─────▶ 3' CGG TAG TTT CGG CCG CA 5'
                                                           A    G        A
                                                                         G 5' GAT  GTT  ACC  CTG  TAT  GG 3' ◀─── oligo(s) NC2
              C    C
              A
              G
```

```
CCCTCGGCGGTAAATGCAAAGCTAAGCGGCTTGGAAAACCCGGCCTGCTTAAATTTCTTAACCAAAAAGGAATACAGCA                    110
                -35                        -10              RBS         Met Lys Lys Ser Leu Ile Ala Leu Thr
                                HaeIII                                    ATG AAA AAA TCC CTG ATT GCC CTG ACT

Ala Ala Leu Pro Val Ala Ala Met Ala Asp Val Thr Leu Tyr Gly Thr Ile Lys Ala Gly Val Glu Thr Ser Arg Ser Val Ala His     200
GCA GCC CTT CCT GTT GCA GCA ATG GCT GAC GTT ACC CTG TAC GGC ACC ATC AAA GCC GGC GTA GAA ACT TCC CGC TCC GTA GCT CAC
signal peptide Gly Ala Gln Ala Asp Arg Val Lys Thr Ala Thr Glu Ile Ala Asp Leu Gly Ser Lys Ile Gly Phe Lys Gly Gln Glu Asp Leu Gly     290
GGA GCT CAG GCG GAT CGC GTT AAA ACC GCT ACC GAA ATC GCT GAT TTG GGT TCG AAA ATC GGC TTT AAA GGC CAA GAA GAC CTC GGC
              Sau3AI                                                                    TaqI Gly Leu Lys Ala Ile Trp Gln Leu Glu Gln Lys Ala Tyr Val Ser Gly Thr Asp Thr Asp Thr Gly Asn Arg Gln Ser Phe Ile Gly     380
GGC CTG AAA GCC ATT TGG CAG TTG GAA CAA AAA GCC TAC GTC AGC GGT ACT GAC ACA GGC AAC CGC CAA TCC TTC ATC GGT Lys Gly Phe Gly Lys Val Arg Val Gly Arg His Val Leu Asn Ser Val Leu Lys Asp Thr Thr Asp Phe Asn Pro Trp Glu Lys Ser     470
AAA GGC GGC TTC GGT AAA GTG CGC GTC GGC CGT TTG AAC AGC GTC CTG AAA GAC ACC ACC GAC TTC AAT CCT TGG GAG AAA AGC Tyr Leu Gly Leu Ser Asn Ile Ala Gln Pro Glu Glu Arg His Val Ser Pro Glu Phe Ala Gly Phe Ala Gly Phe Arg Ala             560
TAT TTG GGT TTA AGC AAC ATT GCC CAA CCC GAA GAA CGC CAC GTT TCC CCC GAA TTT GCC GGC TTC AGG GCA Gln Tyr Val Pro Asn Asp Asn Ser Gly Lys Asn His Ser Glu Lys Asn Tyr Lys Asn Ser Gly Phe Phe Val                          650
CAA TAC GTG CCT AAC GAC AAT TCG GGC AAA AAT CAC AGC GAA TCT TAC AAA AAC AGC GGC TTC TTC GTG Tyr Ala Gly Phe Tyr Lys Arg His Ser Tyr Thr Thr Glu Lys Leu Thr Trp Arg Asn Asp Asn Ser His Asp Ala Leu                 740
TAT GCC GGC TTC TAT AAA AGA CAT AGT TAC ACG ACT GAG AAA CTA ACT TGG CGC AAC GAT AAT TCG CAC AAC TCT GAT GCC CTG Ala Ser Val Ala Val Gln Gln Gln Asp Ala Lys Asp Ala Thr Pro Arg Val Ser Tyr Leu Gly Ser Gln Thr Glu Val Ala Ala Thr    830
GCT TCC GTA GCC GTA CAG CAG CAA GAC GCG AAA GAC GCG ACG CCC CGC GTT TCT TAC CTG GGT TCG CAA ACC GAA GTT GCC GCT ACC Ala Tyr Arg Phe Gly Asn Val Thr Ala His Gly Phe Lys Gly Ser Val Tyr Asp Ala Asp Asn Asp Asn Thr                          920
GCA TAC CGC TTC GGC AAC GTA ACG GCC CAC GGC TTC AAA GGT TCG GTT TAT GAT GCA GAT AAC GAC AAT ACT Asp Gln Val Val Gly Ala Glu Tyr Asp Phe Ser Lys Arg Thr Ser Ala Leu Val Ser Ala Gly Trp Leu Gln Arg Gly Lys Gly        1010
GAC CAA GTG GTC GGT GCG GAA TAC GAC TTC TCC AAA CGC ACT TCT GCC TTG GTT TCT GCC GGT TGG TTG CAA AGA GGC AAA GGC Glu Lys Phe Val Ala Thr Val Gly Gly Val Gly Leu Arg His Lys Phe
GAA AAA TTC GTA GCG ACT GTC GGC GGT CTG CGC CAC AAA TTC TAA TCTGCAAGATC  1076
                                                                Sau3AI
```

```
GATTCCACACACAAAAACAGGCAGAAGTTTGTTTTTTCAGACAGGAACATCTATAGTTTCAGACATGTAACCGCCGAGCCCCTCGGCGGGTAAATGCAAAGTAAGGGCTTGAAAGCCCGG     1
HinfI                                                                                                            -35
                                  signal peptide
           RBS          M  K  K  S  L  I  A  L  T  L  A  A  L  P  V  A  A (T) A  D  V  T  L  Y  G  A  I  K       2
CCTGCTTAATTTCTTAACCAAAAAGGAATACAGCAATGAAAAAAATCCCTGACTTTGGCAGCCCTTCCTGTTGCGGCAACGGCCGATGTCACCCTGTACGGTGCCATCAA A  G  V  Q  T  Y  R  S  V  E  H  T  D  G  K  V  S  K  V  E  T  G  S  E  I  A  D  F  G  S  K  I  G  F  K  G  Q  E  D  L    36
AGCCGGCGTACAAACTTACCGTTCTGTAGAACATACAGACGGAAAGGTAAGTGAAGTGGAAACCGGCAGCGAAATCGCCGACTTCGGTTCAAAAATCGGCTTCAAAGGCCAAGAAGACCT G  N  G  L  K  A  V  W  Q  L  E  Q  G  A  S  V  A  G  T  N  T  G  W  G  N  K  Q  S  F  V  G  L  K  G  G  F  G  T  I  R    48
CGGCAACGGTCTGAAGGCCGTTTGGCAGTTGGAACAAGGTGCCTCCGTCGCCGGCACTAACACCGGCTGGGGCAACAAACAATCCTTCGTCGGCTTGAAGGGCGGCTTCGGTACCATCCG
                                                                                                          KpnI
 A  G  S  L  N  S  P  L  K  N  T (D)(D) N  V  N  A  W  E  S  G  K  F  T  G  N  V  L  E  I  S  G  M  A (K) R  E  H  R  Y    60
CGCCGGTAGCCTGAACAGCCCCCTGAAGAACACCGACGACAACGTCAATGCTTGGGAATCCGGCAAATTTACCGGCAATGTGCTGGAAATCAGCGGAATGGCCAAACGGGAACACCGCTA
                                                                                                  Hinfl L  S  V  R  Y  D  S  P  E  F  F  A  G  F  S  G  S  S  V  Q  Y  A  P  K  D  N  S  G  S  N  G  E  S  Y  H  V  G  L  N  Y  Q  N    72
CCTGTCCGTACGCTACGATTCTCCGGAATTCGCCGGCTTCAGCGGCAGCGTACAATACGCACCTAAAGACAACAATTCAGGCTCAAACGGCGAATCTTACCACGTTGGCTTGAACTACCAAAA S  G  F  F  A  Q  Y  A  G  L  F  Q  R  Y  G  E  G  T  K  K  I  E  Y (E)(H) Q (V) Y  S  I  P  S  L  F  V  E  K  L  Q  V    84
CAGCGGCTTCTTCGCACAATACGCCGGCTTGTTCCAAAGATACGGCGAAGGCACTAAAAAAATCGAATACGAACATCAAGTTTATAGTATCCCAGCCTGTTGTTGAAAAACTGCAAGT H  R  L  V  G  G  Y  D  N  N  A  L  Y  V  S  S  V  A  A  Q  Q  Q  D  A  K  L  Y (Q)(N)(O)(L)(V)(R)(D) N  S  H  N  S  Q  T    96
TCACCGTTGGTAGGCGGTTACGACAACAATATGCCCTGTACGTCTCCGTAGCGCGCACAACAAGATGCCAAATTGTATCAAATTCAATTAGTGCGTGATAATTCGCACAACTCTCAAAC E  V  A  A  T (V) A  Y  R  F  G  N  V  T  P  R  V  S  S  Y  A  H  G  F  K  G  T  V  D  S  A (D) H  D  N  T  Y  D  Q  V  V   1080
CGAAGTTGCCGCTACCGTGCCATACCGTTCGGCAATGTCACGCCCGCGTTCTTCAAGCCAACGGCTTCAAAGGCACTGTTGATAGTGCAGACACGACAATACTTATGACCAAGTGGT V  G  A  E  Y  D  F  S  K  R  T  S  A  L  V  S  A  G  W  L  Q (E) G  K  G  A  D  K  I  V  S  T  A  S  A  V  V  L  R  H    1200
TGTCGGCGCGGAATACGACTTCTCCAAACGCACTTCTGCCTTGGTTTCTGCCGGCTGGTTGCAAGAAGGCAAAGGCGCAGACAAAATCGTATCGACTGCTCCAGCGCCGTCGTTCTGCGCCA K  F
CAAATTCTAATCTGCAAAGATC   1222
           Sau3AI
```

*FIG. 9*

PRODUCTION OF GONORRHEAL PI PROTEINS AND VACCINES

This application is a continuation of application Ser. No. 07/983,995 filed Dec. 1, 1992, U.S. Pat. No. 5,736,361, which is a file wrapper continuation of application Ser. No. 07/689,663 filed Apr. 23, 1991, now abandoned, which is a file wrapper continuation of application Ser. No. 07/242,758 filed Sep. 9, 1988, now abandoned, which is a continuation-in-part of application Ser. No. 07/124,727 filed Nov. 24, 1987, now abandoned.

INTRODUCTION

Gonorrhea is at the present time one of the most widespread venereal disease worldwide, with several million cases occurring in the United States alone each year. The causative agent of the disease is the gonococcus *Neisseria gonorrhoeae*, a bacterium which has throughout its history developed resistance both to traditional antibiotic treatment, and to some extent to the bactericidal activity of normal human serum. The present inability to control the infection by traditional means has made the development of a vaccine which can effectively prevent the infection of utmost importance. The present invention provides a DNA sequence coding for a specific *N. gonorrhoeae* outer membrane protein; the cloned product of this particular DNA sequencie provides a suitable basis for such a vaccine. The present invention also provides species-specific oligonucleotide sequences useful as diagnostic probes for the detection off gonorrheal infection.

BACKGROUND OF THE INVENTION

Vaccines

The production of a protective immune response against any given infection agent in vertebrates depends initially on the provision of the appropriate stimulus to the host's immune system. The infectious organism itself typically provides numerous stipulatory compounds, or antigens, by the very nature of its cell membrane composition, or by the metabolic products it releases in the host's body. These substances, usually larger molecules such as proteins, lipopolysaccharides or glycoproteins, are recognized by the immune system as foreign, and provoke one or more different types of reaction from the host in an effort to remove or disable the invading organism. The antigen may cause production of sensitized lymphocytes (T-cells) which provide a cell-mediated immunity. Alternatively, an antigen may stimulate the synthesis and release of free antibody into the blood and other bodily fluids (humoral immunity). The development of the body's protective immune response depends upon achieving a threshold level of stimulation of one or both of these systems.

A temporary immunity against infection can in many cases be provided by giving an individual preformed antibodies from another individual of the same or different species. This is known as passive immunity. One example of such immunity is the protection afforded to a fetus and newborn by placental transfer of maternal antibodies, as well as transfer of antibodies through milk. Another example is the pooled adult gamma globulin frequently used to prevent or modify the effects of exposure to measles, chicken pox, hepatitis, smallpox and tetanus. These acquired antibodies, however, are gradually utilized by interaction with the antigen or catabolized by the body, and thus the protection is eventually lost.

A more permanent form of protection is afforded by active immunization. Vaccination confers an active protective immunity by employing a harmless or nonvirulent form of the antigen (e.g., a killed or genetically altered bacterium, or an isolated glycoprotein from the cell wall) as a primary stimulus to the immune system. This provokes a rather slow response in antibody production which peaks and falls off. However, the body has been alerted to the existence of the antigen, and the next time exposure occurs, presumably with the live, virulent organism, a secondary response, with a much more rapid and abundant production of antibodies is observed. This secondary response will typically be sufficient to prevent the microorganism from establishing itself sufficiently to be able to cause a full-blown infection.

A vaccine may take a variety of forms, some of which are more effective than others in conferring the protective effect desired. Historically many vaccines have been prepared by killing or inactivating the microorganism causing the disease of interest, and using the killed cells as the active immunogenic agent. Vaccines of this type have been used against typhoid, cholera and poliomyelitis (Salk vaccine). The problem with this type of vaccine is that the treatment required to kill the microorganisms, such as formaldehyde, may frequently alter or destroy the microbe's useful antigens, and thus poor or incomplete immunity may be obtained.

An alternate form of vaccine is that which employs attenuated microorganisms. An attenuated microorganism is one which is still living, and capable of multiplying in the body after administration, but which has either been modified in some way to render it avirulent, or else is a strain which is virulent in other microorganisms, but avirulent in man. The advantage obtained by using an attenuated organism is that the attenuation usually does not affect its antigenicity, thereby providing a more efficient stimulus to the immune system. Attenuated vaccines for measles, rubella and poliomyelitis (Sabin vaccine) have achieved widespread use. Attenuation is typically achieved by altering the growth conditions of the microorganism, or, more recently, genetically modifying the organism's virulence. Although generally more effective than killed vaccines, however, there is danger involved in the possibility of the live organisms reverting to virulence, thereby causing disease symptoms.

Because of the problems associated with whole organism vaccines, it has become more common in recent years to employ individual protective antigens as the active agent in vaccine compositions. Although isolation and identification of the particular antigens of an organism which do stimulate a protective response is not always simple, once identified, this method provides an effective alternative to the whole organism vaccines, without the attendant disadvantages.

Examples of types of antigens which are typically useful for this purpose are purified cell or capsid components, such as bacterial toxins (which must be detoxified to yield a toxoid), bacterial or viral toxin subunits, cell wall polysaccharides, or capsid glycoproteins. These components are often highly effective in producing immunity, but difficulties arise in the actual purification. It is critical that the antigen of interest be isolated more or less completely from extraneous cellular materials, the presence of which can frequently cause an adverse immunologic or metabolic response concurrent with the desired immunity producing reaction. The purification processes required are frequently complex, tedious and prohibitively expensive and the results not always completely predictable. This problem can in some case be avoided by synthetic preparation of small peptide sequences which correspond to epitopes on a microbial antigen. There are, in some circumstances, drawbacks to this technique in that, although the amino acid sequence corresponds to the natural epitope sequence, the conformation may not be sufficiently similar to that of the parent antigen to elicit the appropriate immune response.

Many of the disadvantages attendant upon these aforementioned vaccine types may be avoided by the use of recombinant DNA technology. The possibility of cloning genes which code for all or part of an important microbial antigen provides a relatively economical and convenient source of larger amounts of the necessary immunogenic material, substantially free of contaminating proteinaceous or genetic material. In brief, this method of producing purified antigens involves the insertion of the specific DNA sequence coding for the antigen into a DNA vector to form a recombinant DNA molecule which can be replicated by a host cell. There is now an abundance of methods by which recombinant DNA molecules may be prepared. One of the better known techniques is that described by Cohen and Boyer in U.S. Pat. No. 4,237,224, the teachings of which are herein incorporated by reference. In this method recombinant plasmids are produced using restriction enzyme and ligation; the resulting plasmids are then placed into a unicellular host cell which is thereby transformed, and begins replication of the foreign DNA. Another method, utilizing bacteriophage vectors, is described in U.S. Pat. No. 4,304,863, also incorporated herein by reference. The cloning method provides the greatest potential for making convenient, economical sources for vaccine preparation readily available; it is not without difficulties, however, in that the appropriate gene for an antigen known to be immunogenic must first be isolated and sequenced, inserted into a plasmid in such a way as to insure proper replication, transcription and translation, and then inserted into a compatible host cell.

The potential for failure of the expression of the desired gene product is tremendous if any one of transcription of the gene, translation of the RNA, or post-translational processing and compartmentalization of the polypeptide is not performed correctly. For a cloned insert to be transcribed, it is necessary that there is present a promoter which the host rNA polymerase can recognize. Proper translation requires that the RNA has a ribosome binding site. Post-translational modification of proteins often involves cleaving of a signal sequence which functions by directing the protein out through the cell membrane. Degradation of the foreign protein produced by the host microorganism may also occur if the configuration or amino acid sequence does not protect them from the action of the host's intracellular proteases. Thus, although conceivably the ideal way of ultimately constructing a Neisseria vaccine, these techniqes have not previously been applied to vaccine preparation for gonorrhea.

Gonococcal Antigens

Some antigens of Neisseria gonorrhoeae have been extensively studied and classified. Gonococcal pili, for example, have been found to be antigenic (Buchanan et. al., J. Clin. Invest. 52:2896–2909, 1973), consisting primarily of a protein subunit of about 20,000 M.W. A synthetic form of this material has been formulated into a vaccine preparation (Schoolnik et al., Prog. Allergy 33:314–331, 1983). The lipopolysaccharide of N. gonorrhea is also antigenic, with the β-1, 4-linked galactose-glucose residues being the principal determinant. The greatest concentration of study in this area in recent years, however, has probably been focused on the outer membrane proteins, a complex of proteins whose role in immunogenicity is not yet fully understood. The composition of the outer membrane protein is known to vary somewhat from strain to strain, and on this basis at least 16 different serotypes have been identified (Johnston et. al., J. EXP. Med. 143:741–758, 1976). A number of vaccine compositions employing portions of the gonococcal membrane have previously been described, for example, in U.S. Pat. No. 4,203,971, U.S. Pat. No. 4,288,557 and U.S. Pat. No. 4,681,761. Most of these compositions, however, contain a mixture of protein and other material, and all require fairly elaborate purification procedures for isolation and separation of the active components from the bacterial cell. Thus, these vaccines may not have the desired immunospecificity, and also require a tremendous amount of microbial source material in order to produce commercial quantities of the product.

Gonococcal Protein I

Also suggested as a possible candidate for the basis of a vaccine composition is the specific outer membrane protein known as Protein I, or PI. PI is the major outer membrane protein of N. gonorrhoeae, functioning as a porin (Douglas et al., FEMS Microbiology Letters 12:305–309, 1981), a protein which is believed to operate in the cell by channelling low molecular weight substances across the hydrophobic lipid outer membrane. There are a number of features which make PI an interesting focus of attention: First, it is at least partly responsible for serotype specificity in Neisseria, and there are a relatively small number of antigenic serotypes of Protein I. Also, a number of gonococci possessing particular PI serotypes have been associated with complicated gonococcal infections. Further, it appears to be surface exposed in its native state, and also appears to stimulate the production of opsonins (Sarafian et al., J. Infect. Dis. 148:1025–1032, 1983). Opsonins are antibodies which bind to the surface of an infectious organism, facilitating the engulfment of the organism by phagocytes. Its immunogenic potential has already been demonstrated in vaccinated mice (Jiskoot et al., Infect. Immun. 54:333–338, 1986).

Two different major types of PI molecules have been demonstrated in gonococci, PIA and PIB (Barrera et al., Infect. Immun. 44:565–568, 1984), based on peptide mapping and susceptibility to proteolysis (Blake et al, Infect. Immun. 33:212–222, 1981). This division has been found to correlate with serogroup patterns (Sandstrum et al., Infect. Immun. 35:229–239, 1982; Sandstrum et al., Infect. Immun. 38:462–470, 1982) and pathogenesis. Gonococci expressing protein IA are associated with systemic infections, while those with protein IB are associated with localized infection (Buchanan et al., Infect. Immun. 32:985–994, 1981; Hildebrandt et al., Infect. Immun. 20:267–273, 1978).

Despite all the attention paid to developing PI as a potential vaccine candidate, there has not yet been produced an effective vaccine based on PI. Further, there has not yet been any elucidation of the gene sequence controlling its production, and little is known about the protein's structure. The present invention provides the first description of a full PI gene sequence, that of the PIA structural gene, as well as a cloned gene product. Also described is a novel PIB gene sequence, as well as unique PIA-PIB chimeras derived from these sequences. The latter chimeras are useful in epitope napping as well as being a basis for vaccine development.

Diagnostic Probes

Another aspect of the widespread nature of this disease is the importance of early detection and diagnosis. There are, of course, standard bacteriological tests available for diagnosis of gonorrhea, but such tests rely on the growth of bacteria in culture which can be time consuming, and which is also generally rather non-specific. Neisseria gonorrhoeae is known to have different serotypes, which may be indicative of very distinct patterns of the disease, as noted in the previous section. In order to effect the appropriate treatment for the disease, it is critical that diagnosis not only be rapid, but also as accurate as possible.

The development of DNA- and RNA-probe technology has provided a solution to many such problems in diagnosis. A probe is typically a radiolabelled single strand of DNA or RNA which is complementary to all or a portion of a particular gene of interest, and therefore, when exposed to a single strand of the complementary nucleic acid, will hybridize to it. Probes are employed in a technique known as Southern blotting, in which DNA fragments from a sample suspected of containing the gene of interest are separated in agarose gels, denatured to create single strands, and then transferred to nitrocellulose filters. Here they are incubated with labelled, pre-selected probes, which will hybridize to a complementary strand and thus identify, by its label, the presence of the desired gene. Such probes can also be usefully employed in the identification of a particular clone containing a gene of interest from a genomic library established by cloning DNA fragments of an entire genome in host cells.

There has not heretofore been a convenient and highly accurate probe system developed in connection with Neisseria gonorrhoeae. The present invention, however, provides the first development of several oligonucleotide probes for N. gonorrhoeae, certain of which will hybridize generally to Protein I of N. gonorrhoeae but not to other bacteria, and others which are specific for N. gonorrhoeae serotypes which express the PIA antigen only. Thus is provided a reliable diagnostic method for detecting gonococcal infection, as well as identification of the particular category of serotype in which an individual may be infected.

SUMMARY OF THE INVENTION

The complete nucleotide sequence for the Protein IA, and for Protein IB, of Neisseria gonorrhoeae is described, as well as their predicted amino acid sequences. Also described are methods and compositions for the cloning and expression of the PIA and PIB gene in a single cell host organism, as well as cloning and expression of PIA-PIB chimeric protein products. Also described are methods for culturing the novel host organism so as to produce the gene products. The products of the recombinant DNA methods employed are suitable for use in whole or in antigenic part, as immunogens in vaccine compositions to prevent gonorrhea.

The PIA and PIB genes were isolated from the bacterial genome by hybridization of DNA fragments with novel oligonucleotide probes once localized in a specific segment of DNA, the nucleotide sequence was determined and the amino acid sequence was predicted. Each gene was then inserted into a plasmid cloning vector which functions as the unit of replication of the gene. The recombinant plasmid was then used to transform a compatible host cell, whereby the gene product is expressed. Methods are also described herein which permit the isolation of the expressed products and the formulation of each into a vaccine composition. In particular, vaccine compositions comprising a hybrid PIA/PIB protein are also proposed. Based on the determination of nucleotide sequences of the PIA and PIB gene, the invention also provides the sequence of oligonucleotide probes which are useful in the detection and diagnosis of gonococcal infection. In this regard, the invention also contemplates diagnostic test kits comprising one or more of the oligonucleotide probes disclosed herein.

DESCRIPTION OF FIGURES

FIG. 1. Amino acid sequence of residues 1 through 12 of PI of strain R10, the encoding mRNA sequence including degenerate bases, and the oligonucleotides synthesized. Where degeneracy occurred, sequences were chosen based on codon usage data from other sequenced gonococcal genes.

FIG. 3. DNA sequence of the PI gene of FA19. The predicted amino acid sequence is shown above the DNA sequences (−35 and −10) and ribosome binding site (RBS) are shown, as are the TaqI and Sau3AI sites and the HaeIII site used in the construction of pUNC7. The last base number of each line is shown on the right.

FIG. 9. DNA sequence of the PIB gene of MS11. The predicted amino acid sequence is shown above the DNA sequence, with the signal peptide indicated. The putative promoter sequences (−35 and −10) and the ribosome binding, site (RBS) are shown, as are the relevant restriction enzyme sites. The last base number of each line is shown on the right. To denote differences from the PIB sequence of R10, (Gotschlich et al., PNAS USA 84:8135–8139, 1987), bases (other than those comprising a restriction enzyme site) are underlined and amino acids are circled.

DESCRIPTION OF THE INVENTION

Figure 2:
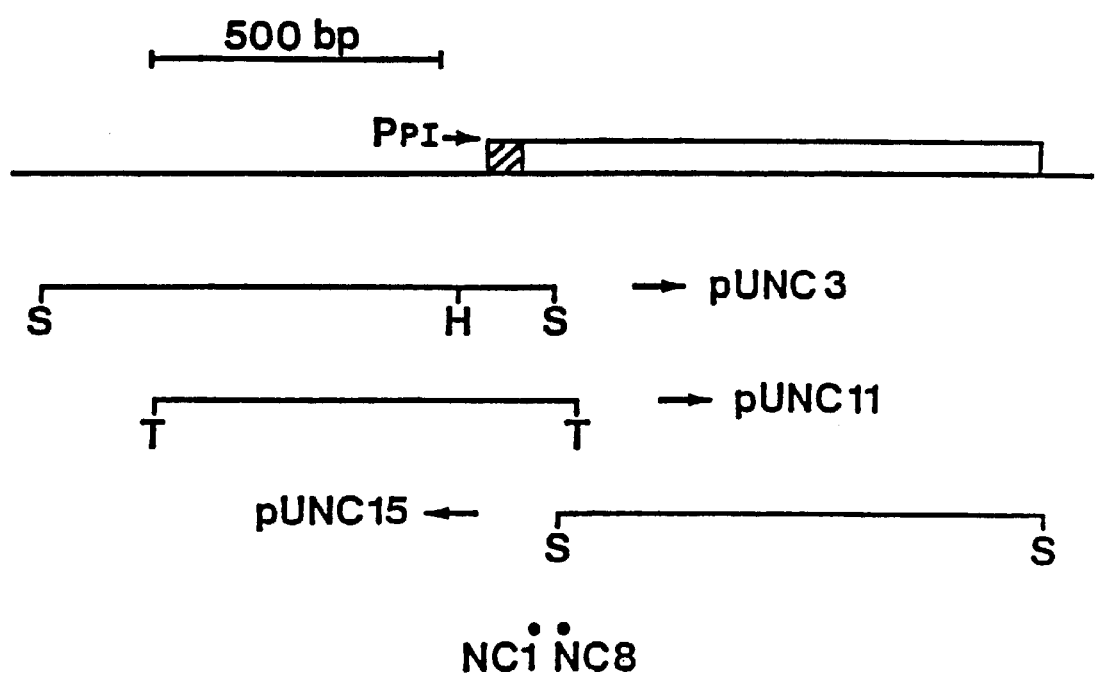
FIG. 2. Sau3AI and TaqI fragments of FA19 genomic DNA including portions of the PI gene. Fragments were cloned into the vector plasmid pGEM-2, resulting in recombinant plasmids with the designations shown here. The relative position of the PI coding region on the genome is indicated by the open box above (the shaded box corresponds to the N-terminal signal sequence) and the relative position of the oligonucleotide probes is shown below the fragments.

This invention relates to the use of N. gonorrhoeae PIA, PIB, and chimaeric PIA/PIB proteins which are useful in the preparation of a vaccine composition for the prevention of gonorrheal infection. These proteins may be produced by recombinant DNA techniques or chemical synthetic techniques. Although it has previously been possible to use chemical isolation techniques from an appropriate N. gonorrhoeae strain, the latter may result in contamination by certain other gonococcal proteins that elicit blocking (anti-protective) antibodies after vaccination. Since the PI proteins are known to stimulate the production of antibodies, it is possible to employ the whole proteins or any immunogenic portion thereof, as immunogens which would effectively protect the recipient from infection by N. gonorrhoeae.

The recombinant plasmids described herein enable the production in a host cell of large quantities of the PI proteins which are stable and resistant to host cell degradation, thereby providing an abundant source of suitable material for vaccine compositions. This preparation is free of contamination by other anti-protective gonococcal proteins. For purposes of description only the invention is discussed below in several individual steps, comprising 1) identification and isolation of the PIA gene or gene fragment; 2) insertion of the gene or gene fragment into a suitable cloning vehicle which is used to transform a compatible host cell; 3) identification and growth of the transformed host cells replicating and expressing the gene; and 4) identification and purification of the gene product. In accordance with the invention PI proteins may be produced by inserting the cloned sequence of FIG. 3 or FIG. 9, or hybrids thereof into an appropriate cloning/expression vector, transforming appropriate host cells and identifying and purifying the gene product. Alternatively, portions of the deduced amino acid sequence, of FIG. 3 or FIG. 9, or hybrids, may be synthesized using chemical synthetic techniques well known in the art. Also disclosed herein are oligonucleotides based on the PIA and PIB sequences, which oligonucleotides are useful in identification and diagnosis of N. gonorrhoeae infection by hybridization techniques such as Southern blot, dot blots, slot blots, etc.

Identification, Isolation and Sequence of the Pia Gene

The nucleotide coding sequence for the PIA protein is depicted in FIG. 3. As already noted, the PIA protein is not produced by all N. gonorrhoeae; any given strain will produce either PIA or PIB, but not both. The presence of PIA is correlated with gonococcal serogroup I, serotype 1–3, and thus any of those strains associated with serotypes 1–3 may be employed as the source of PIA DNA. Among the known N. gonorrhoeae strains which are characterized by PIA are FA19, FA130, W-Ue, B-2, G-7, 5029, R-11, E-5, D-4, V-15 (Knapp et al., J. Inf. Dis. 150:44–48, 1984). In the practice of the invention, the sequence depicted in FIG. 3 can be obtained in a variety of ways. For example, once a suitable PIA-containing strain is determined, it is necessary to isolate the organism's DNA, generate DNA fragments, and identify the fragments which contain the PIA gene sequence. Alternatively, the gene or segments of the gene could be synthesized.

The N. gonorrhoeae DNA may be fragmented in a number of different ways; the most preferred method is by its treatment with restriction enzymes, each of which cleaves the DNA at a specific sequence. Other methods include treatment of the DNA with DNase in the presence of magnesium, or physical disruption, such as by sonication. When restriction enzymes are employed, one enzyme or a combination of enzymes may be used to treat the DNA. The only requirement is that the digestion of the nucleic acid does not destroy the region coding for the antigen site or sites of PIA. After fragmentation, the individual fragments of linear DNA are then separated by size by any one of the number of known techniques, such as polyacrylamide gel electrophoresis (PAGE), agarose gels, or column chromatography. Isolated fragments provide the genetic material for plasmid preparation and transformation.

Identification of the DNA fragments containing the gene sequence of interest can be achieved in a number of ways. For example, immunologic reagents, such as monoclonal antibodies, may be used. A number of monoclonal antibodies to PIA have been raised (Tam et al., Infect. Immuno. 36: 1042–1053, 1982) and these can be used to test the products produced by each of the host cells transformed by the various DNA fragments; a product which reacts with the PIA monoclonal antibody identifies the cell which has been transformed with the fragment containing the PI gene. Alternately, sequencing of the DNA fragments permits the prediction of an amino acid sequence of each, and comparisons can then be made with any known partial amino acid sequences to identify the fragment containing the corresponding DNA sequence. Another popular technique is Southern blotting (Southern, *J. Mol. Bio.* 78:503, 1975). In this method, the restriction fragments are denatured in position on a gel and transferred to a solid substrate, typically a nitrocellulose filter, by blotting. The filter is then exposed to radiolabelled oligonucleotides containing a known or presumed partial DNA sequence for the protein. The blotted DNA, complementary to the selected oligonucleotide will hybridize to it, thereby identifying the size of the DNA fragment containing the PI gene.

In the examples detailed below, the gene coding for PIA was identified and isolated by hybridization with two novel oligonucleotides. Based on the known sequence (Blake et al., *Infect. Immun.* 36:277–285, 1982; Blake in *The Pathogenic Neisseria*, G. Schoolnik, ed., 251–258, 1985, ASM) of a small portion of the N-terminal amino acids of PIB, end codon usage rules implied in various other gonococcal proteins with known DNA sequences, an attempt was made to deduce useful oligonucleotides. In particular, two sequences, designated NC1 and NC2, were constructed as follows:

```
NC1: 5' AC GCC GGC TTT GAT GGC 3'

NC2: 5' GAT GTT ACC CTG TAT GG 3'
          C   C           C
          A
          G
```

Employed in a Southern blot hybridization, the foregoing oligomers were used to screen the DNA restriction fragments obtained from the gonococcal genome; both probes were successful in identifying DNA fragments containing the PIA. gene. Verification of the identified gene as the PIA gene was made by comparison of the gene product's molecular weight with that of the native protein, and by its immunoreactivity with PIA-specific monoclonal antibodies. In addition to this utility, however, it has also been determined that each of these cligonucleotides has the ability to hybridize with both PIA and PIB strains of gonococci. Thus, these normal compounds can also be used as diagnostic probes, in a Southern blot hybridization, for the detection and identification of *N. gonorrhoeae* infection in afflicted individuals.

Identification of the fragments containing the PI gene is followed by sequencing of the relevant portion, according to the method of Sanger (*PNAS USA* 74:5463–5467, 1977). The Sanger method employs enzymatic synthesis of a complementary strand of DNA from a DNA template. The synthesis of the complementary strand is terminated by the incorporation of a dideoxynucleotide (ddNTP). Four separate reactions are performed, each containing ddATP, ddCTP, ddGTP, or ddTTP, so that four sets of DNA fragments are generated, and each one within a given set will terminate with the specific dideoxynucleotide. The DNA fragments are then separated on a polyacrylamide gel; the sequence is determined by knowledge of the identity of the last nucleotide in each fragment, and reading from the shortest to the longest fragment.

The single stranded DNAs which are used as templates may be provided by chemical treatments of double stranded DNA's with exonucleases. However, it is more efficient to employ the M13mp cloning vectors, as developed by Messing et. al. (*Nucleic Acids Res.* 9:309, 1981) as a cloning vector. M13 is a male-specific filamentous bacteriophage of *E. coli* which contains a single (+) stranded DNA. The (+) strand is used as a template for the synthesis of the complementary (−) strand. The double stranded form of DNA is the replication form, or RF, which is amplified to about 200 copies per cell. This double stranded form can be isolated from cells and used as a cloning vector. Once amplification stops, only one of the two strands continues to be produced, and a single strand is incorporated into the phage particles. Herein lies the advantage of M13, in that particles have a single strand of DNA which is homologous to one of the cloned strands, and therefore can be useful as the template in the Sanger method Up to 350 bases can be sequenced from a single clone, and sequencing of longer fragments can be achieved by sequencing overlapping fragments.

Utilization of the foregoing technique has provided the nucleotide sequence of the PIA gene, which is reproduced in FIG. 3. Also provided in FIG. 3 is the predicted amino acid sequence.

The sequencing of the PIA gene, which was achieved by separate sequencing of overlapping fragments, also permitted the identification and preparation of two other oligonucleotide probes. Both probes are 17 nucleotide oligomers having the following sequences:

NC8: 5' GCGTTAAAACCGCTACC 3' and

NC11: 5' CGGTGTCGGTCTGCGCC 3'

These probes are both specific to PIA genes alone, and do not hybridize with PIB DVA sequences. Thus, each of these probes is useful in diagnostic testing for differentiation between infections with PIA organisms, and PIB organisms. As previously noted, each of these proteins is indicative of a specific pattern of gonorrhea infection, either systemic or localized, and therefore may be extremely important in planning a program of treatment of the afflicted individual.

The isolated gene, or a chemically synthesized DNA sequence, can be employed to generate additional copies of the gene by growth of transformed host cell organisms isolation of the recombinant DNA from the transformed cells, and recovering the inserted gene from the isolated recombinant DNA.

Identification, Isolation and Sequence of the PIB Gene

A nucleotide sequence for a PIB protein is depicted in FIG. 9. The sequence shown was isolated from *N. gonorrhoeae* strain MS11. The presence of PIB is correlated with serogroups 4–9, and any strains associated with those serogroups may be used as a source of PIB DNA. Among the known gonorrheal strains which are characterized by the presence of PIB are MS11, FA6140, F62, and R10. The techniques for preparation, identification, and sequencing of the PIB protein are substantially identical to those applied to the PIA protein described above in Section 5.1. The specific identification of the PIB gene was aided by the use of the NC1 and NC12 probes (5'-GATACGGCGAAGGCATC-3') and identification of a KpnI restriction site in the PIB portion of a hybrid PI protein (Danielsson et al., *Infect. Immun.* 52:529–533, 1986). Cloning of the gene, like PIA, was achieved by separate cloning of overlapping sequences in a cloning vector.

Production of PIA, PIB or PIA/B Hybrids by Recombinant DNA Techniques

The nucleotide coding sequence for PIA is depicted in FIG. 3. The nucleotide coding sequence for PIB is depicted in FIG. 9. In the practice of the method of the invention, either nucleotide sequence, or its functional equivalent can be built into recombinant molecules which will direct the expression of the PIA or PIB product, respectively. Hybrid sequences derived from both FIG. 3 and FIG. 9 can also be constructed for the production of hybrid PIA/B proteins.

Due to the degeneracy of the nucleotide coding sequences, other DNA sequences which encode substantially the same amino acid sequence as depicted in FIG. 3 or FIG. 9 may be used in the practice of the present invention for the cloning and expression of PIA or PIB, respectively. Such alterations of the nucleotide sequence of FIG. 3 or FIG. 9 include deletions, additions or substitutions of different nucleotide residues resulting in a sequence that encodes the same or a functionally equivalent gene product. The gene product may contain deletions, additions or substitutions of amino acid residues. Substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

Preparation of A PI Gene Cloning/Expression Vector

The PIA gene sequence depicted in FIG. 3 or the PIB sequence depicted in FIG. 9 as well as hybrid PIA/B sequences, or functional equivalents thereof, may be inserted into a suitable cloning expression vector.

In order to eventually achieve transcription and translation of the inserted gene, the gene must be placed under the control of a promoter compatible with the chosen host cell. A promoter is a region of DNA at which RNA polymerase attaches and initiates transcription. The promoter selected may be any one which has been isolated from the host cell organism. For example, $E.$ $coli$, a commonly used host system, has numerous promoters such as the lac or recA promoter associated with it, its bacterio-phages or its plasmids. Also, synthetic or recombinantly produced promoters, such as the $\lambda$ phage $P_L$ and $P_R$ promoters may be used to direct high level production of the segments of DNA adjacent to it.

An initiation signal is also necessary in order to attain efficient transcription and translation of the gene. For example, in $E.$ $coli$, mRNA, a ribosome binding site includes the translational start codon (AUG or GUG) and another sequence complementary to the bases of the 3' end of 16S ribosomal RNA. Several of these latter sequences (Shine-Dalgarno or S-D) have been identified in $E.$ $coli$ and other suitable host cell types. Any SD-ATG sequence which is compatible with the host cell system, can be employed. These include, but are not limited to, the cro gene or N gene of coliphage lambda, or the $E.$ $coli$ tryptophan E, D, C, B or A genes.

A number of methods exist for the insertion of DNA fragments into cloning vectors in vitro. DNA ligase is an enzyme which seals single-stranded nicks between adjacent nucleotides in a duplex DNA chain; this enzyme may therefore be used to covalently join the annealed cohesive ends produced by certain restriction enzymes. Alternately, DNA ligase can be used to catalyze the formation of phosphodiester bonds between blunt-ended fragments.

Finally, the enzyme terminal deoxynucleotidyl transferase may be employed to form homopolymeric 3'-single-stranded tails at the ends of fragments; by addition of oligo (dA) sequences to the 3' end of one population, and oligo (dT) blocks to 3' ends of a second population, the two types of molecules can anneal to form dineric circles. Any of these methods may be used to ligate the gene segment promoter and other control elements into specific sites in the vector. Thus, the gene coding for the PI proteins is ligated into the chosen vector in a specific relationship to the vector promoter and control elements, so that the sequence is in the correct reading frame with respect to the vector ATG sequence. The vector employed will typically have a marker function, such as ampicillin resistance or tetracycline resistance, so that transformed cells can be identified. The method employed may be any of the known expression vectors or their derivatives; among the most frequently used are plasmid vectors such as pBR 322, pAC 105, pVA 5, pACYC 177, PKH 47, pACYC 184, pUB 110, pmB9, pBR325, Col El, pSC101, pBR313, pML21, RSF2124, pCR1 or RP4; bacteriophage vectors such as lambda gt11 lambda gt-WES-lambdaB, Charon 28, Charon 4A, lambda gt-1-lambda BC, lambda-gt-1-lambda B, M13mp7, M13mp8, M13mp9; SV40 and adenovirus vectors, and yeast vectors.

Identification and Purification of the PIA and PIB Gene Products

As already noted the gene segments coding for PIA and PIB were originally identified by hybridization with the novel oligonucleotide sequences described above. The identity of the selected fragment as the structural gene coding for PIA was verified both by molecular weight comparison with native PIA, and by the product's reacting with all six tested PIA monoclonal antibodies in a colony radioimmunoassay. The identity of the PIB product was also verified by reaction with PIB-specific monoclonal antibodies. $E.$ $coli$ host cells expressing the cloned PIA or PIB gene produce abundant PI protein that reacts with the appropriate monoclonal antibodies. A purification procedure for the PIA protein is described in detail in Teerlink et al. (in *The Pathogenic Neisseria*, G. Schoolnik, ed., 259–264, 1985, ASM).

Preparation of PIA/B Hybrids

Also created in connection with the present invention are a number of hybrid PIA/B gene sequences and proteins. The hybrid genes were constructed by utilizing the method of shuttle mutagenesis modified after Seifert et al. (*Genetic Engineering, Principles and Methods*, Vol. 8, p. 123–134, Settin et al., eds., Plenum Press, 1986; *PNAS USA* 83:735–739, 1986), to insert a selectable iaarker adjacent to the PI gene in a PIA producing strain. In this case, the selectable marker was the chloramphenicol acetyl transferase (CAT) gene, which confers a selectable chloramphenicol resistance (Cm'). The PIA strain containing the CAT DNA was then used as a DNA donor to transform a PIB containing recipient strain. The reciprocal cross was also performed. Putative hybrids were identified by selecting for Cm', and scoring for PI by immunoblotting. Transformants in which either (1) the donor DNA was present, or (2) the recipient DNA was retained, or (3) in which the DNA was distinct from that of either parent, were all observed. The production of truly hybrid PIA/B strains occurred in both types of crosses at a reasonably high frequency, with a number of different serovars being identifiable. The availability of these hybrid genes and proteins has made possible the analysis of the location of the epitopes for the known monoclonal antibodies, and also allows identification, and ultimately synthetic construction of PIA/B hybrid proteins which contain epitopes which are known to induce the production of protection antibodies and therefore are of greatest interest in the development of a useful vaccine. The detailed description of the construction and identification of these hybrids is found in Section 7, below.

Production of PIA, PIB and Hybrid Proteins by Synthetic Techniques

In an alternate embodiment, the proteins encoded by the gene sequence, as depicted in FIGS. 3 and 9, as well as chimaeric proteins containing portions of each, can be readily synthesized chemically, by techniques which are well known in the art (*J. Chem. Soc. Perkin Trans.* I:361, 1986). In ultimate practice, upon identification of the protection epitopes within the protein sequence, peptide synthesis of the isolated active regions of the molecule provides a simple and relatively low-cost method of producing the basic material for vaccine preparation. The use of peptide synthesis also provides a convenient means for the construction of a hybrid PIA/PIB protein, or, preferably, a synthetic peptide comprising protective epitopes of both the PIA and PIB proteins. Thus, the present invention encompasses both recombinantly produced and synthetically produced proteins in accordance with the disclosed sequences. Also encompassed are fragments of the entire protein, particularly fragments which retain the antigenicity of the parent protein molecule, and most particularly, fragments containing epitopes which elicit production of protective antibodies. It will also be recognized that it is possible to make substitutions within the whole protein and peptide fragment sequences, by replacing one or more amino acid residues in the sequence with a chemically equivalent amino acid; for example, negatively charged residues such as aspartic acid and glutamic acid may be interchanged, as may be positively charged residues such as lysine or arginine. Hydrophobic residues include tryptophan, phenylalanine, leucine, isoleucine, valine and alanine. It is also possible to make certain deletions from or additions to the known sequence and still retain the desired antigenic activity. Given the present information regarding the sequence of the two proteins, it is well within the skill in the art to make appropriate alterations in the molecule and to determine if activity is retained. The present invention therefore also contemplates homologues, analogies, and fragments of the claimed proteins, whether cloned or synthetically produced, wherein the antigenicity of the parent molecule is substantially retained.

Formulation of a Vaccine

The gene product in purified form or the synthetic PIA peptide is useful in preparation of a vaccine composition for prevention of gonorrheal infection. Either the whole PIA protein, or any active portion thereof, can be employed as the immunogenic agent in such a composition. If the gene product has been expressed as part of a fusion protein, the protein as a whole may be employed, or the host cell protein may be cleaved to yield the unfused PIA protein.

The PIA protein made by recombinant DNA techniques may be isolated from the host cells by standard protein isolation techniques. The purified protein is then combined with any of the commonly used pharmaceutically acceptable carriers, such as water, physiological saline, ethanol, polyols, such as glycerol or propyleneglycol, or vegetable oils, as well as any of the vaccine adjuvants known in the art. The PIA product may also be incorporated into liposomes for use in a vaccine preparation. As used herein, "pharmaceutically acceptable carriers" is included to encompass any and all solvents, dispersion media, coatings, antibacterial and antifungal agents; isotonic and absorption delaying agents and the like. The use of such agents for pharmaceutically active substances is known in the art. Except insofar as any conventional medium is incompatible with the active ingredient, its use in the therapeutic composition is contemplated. Supplementary active ingredients may also be incorporated.

A particularly useful embodiment of the present invention is a vaccine in which the active immunogen is a hybrid PIA/PIB protein. Experimentally derived recombinant gonococci expressing epitopes of both PIA and PIB have been reported in the literature (Danielsson, *Inf. Immun.* 52:529–533, 1986), but the structure of the chimaeric protein was not identified and there was no suggestion for possible use of the protein in a vaccine. Such a vaccine would provide the advantage of being able to immunize an individual against both types of gonorrheal infection, i.e., systemic infections associated with protein IA-containing strains, and localized infections associated with proteinIA- or proteinIB-containing strains. Given the availability of the specific probes described in connection with the present invention, obtaining such an appropriate hybrid protein can be readily accomplished using techniques known to those skilled in the art.

In principle, a chimaeric gene may be constructed by first isolating the genes for the individual proteins. A method for isolating the PIA gene, using the PIA specific oligonucleotide proteins of the invention has already been described above. Similar procedures may be followed for isolation and identification of the PIB gene. A number of strains have been identified which produce only the PIB protein, e.g., MS11, R10, FA6140, F62, and many others. The non-PIA specific DNA sequences disclosed above can be conveniently used to isolate restriction fragments containing a PI sequence from the PIB-specific strain, from a gene library of PIB strains. Verification of the expression of the correct product can be obtained by transformation and expression of the putative PIB fragment by a host microorganism, and identification of the expressed product by reaction with any of the known PIB specific monoclonal antibodies (R. C. Nowinski, Knapp, J. S., Tam, M. R., and Sandstrom *J. Infect. Dis.*, 150:44–48, 1984). Once each of the individual gene fragments has been isolated, they may be readily cloned and assembled by any of the methods known in the art. Portions of the PIA sequence are then ligated to portions of the PIB sequence in such a manner that a chimaeric protein is encoded in a transcribable and translatable form, e.g., uninterrupted by translation termination sequences. The entire chimaeric sequence may then be ligated into a vector containing a selectable marker and control elements. The vector may then be used to transform a host microorganism which is capable of expressing recoverable quantities of the gene product. Alternately, of course, one may simply use as a starting point a vector already containing the PIA gene, such as the plasmid contained in *E. coli* NRRL B-18263; the PIB sequence is isolated as described above, and ligated in whole or in part into the plasmid, adjacent to or within the PIA gene so as to permit transcription and translation of the desired chimaeric gene. Preferably, however, construction of PIA/B hybrids may be achieved as described above in Section 5.6, the hybrid gene isolated therefrom, and used to create a vector for transformation. The vector so constructed is again used to transform a host microorganism. Expression of the gene product thus provides a source of the chimaeric protein, which may be readily incorporated into a vaccine formulation in the same manner as the PIA or PIB proteins alone.

In an alternate embodiment, however, hybrid protein useful in vaccine formulation is prepared synthetically, by isolation and identification of the protective epitopes on the now known protein sequences. As noted above, the ready availability of recombinant chimaeric proteins has made it possible to more readily identify the epitopes of interest and thereby eventually permit construction of a "streamlined" hybrid containing only those portions of the hybrid protein necessary for producing immunity by synthetic methods.

Example I: PIA Gene Identification, Isolation and Expression

According to the method of the present invention, the PIA gene sequence was determined by obtaining fragments of gonococcal DNA, cloning individual fragments separately, and then reconstructing the gene, with a foreign inducible promoter. Two presumptive fragments containing portions of the PIA gene sequence were identified by hybridization with the oligonucleotide NCI, as earlier described. The relevant restriction fragments were each then ligated into a pGEM-2 plasmid vector and transformed into an appropriate host. Transformants which hybridized to oligo NC1 were isolated. Plasmid DNA was prepared from these clones, digested with the appropriate restriction enzyme and again probed with NC1. The individual fragments which hybridized to NC1 were then separately religated into pGEM-2 plasmids, resulting in two separate plasmids, pUNC3 and pUNC11.

The identity of the DNA sequence of a 750 bp fragment was determined by subcloning smaller restriction fragments from it into M13 mp18RF DNA, and then sequencing according to the method of Sanger (*PNAS USA* 74, 5463–5467, 1977). From this sequence, a new oligonucleotide was synthesized. The new oligonucleotide, designated NC8, was used to identify an 850 bp fragment adjacent to a 900 bp fragment already cloned, and this fragment was cloned into pGEM-2 to give pUNC15, and sequenced by the method of Sanger (supra). The details of the procedures involved in plasmid preparation, sequencing, hybridization and transformation are set forth below.

General Procedures Used for Preparation of the Plasmids

The following subsections describe the general procedure used for DNA isolation, enzyme reactions, isolation of fragments, and ligation reactions.

Conditions for Restriction Enzyme

The restriction enzymes used in the present experiments are obtained from New England Biolabs, Inc., Beverly, Mass. unless otherwise indicated. *N. gonorrhoeae* cultures are grown in GC base medium (DIFCO) containing Kellogg's supplements I and II (*J. Bacteriol.* 85: 1274–1279, 1963), in a 5% $CO_2$ atmosphere. The DNA required for the digestion was isolated from the gonococcal strain FA19, as described in Maness et al. (*J. Infect. Dis.* 128:321–330, 1973), in accordance with the method of Stern et al. (*Cell* 37:447–456, 1984). This strain is known to produce Protein IA.

All digestions were performed under the following conditions: a DNA sample of approximately 20 µl was incubated at 37° C., for 1–3 hours, in a 2–10 fold excess of restriction enzyme. The exceptions to these conditions are a temperature of 65° C. for TaqI, and 30° C. for SmaI.

Restriction Enzyme Buffers

The buffers used for AccI, MspI, and RsaI digestions consisted of:

50 mM Tris-HCl, and 10 mM $MgCl_2$ at pH 8.

The buffer used for AvaI, HaeIII, HindIII, and TaqI digestions consisted of:

50 mM Tris-HCl, 10 mM $MgCl_2$, and 50 mM NaCl, at pH 8.

The buffer used for BamHI, EcoRI, and SalI digestions consisted of:

50 mM Tris-HCl, 10 mM $MgCl_2$, and 100 mM NaCl, at pH 8

The buffer used for HincII, Sau3AI, and SmaI digestions consisted of:

20 mM Tris-HCl, 5 nM $MgCl_2$, and 50 mM KCl, at pH 7.4.

Reactions are stopped by the addition of 0.5 M EDTA (pH 7.5) to a final concentration of 10 mM.

Identification of Relevant Restriction Fragments

Initial attempts at cloning PIA in pBR322 on other vector plasmids in *E. coli* strain HB101 (Maniatis et al., *Molecular Cloning*, Cold Spring Harbor Laboratory, Cold Spring Harbor, N.Y., 1982), were repeatedly negative. It was therefore decided to attempt to identify fragments containing the PIA gene, or a portion thereof by hybridization with oligonucleotide probes. Two probes were designed based on the known N-terminal amino acid sequence of PIB of *N. gonorrhoeae* strain R10 (Blake et al., *Infect. Immun.* 36:277–285, 1982). In conjunction with a limited amount of codon usage data obtained from the gene sequences of pilin (Meyer et al., *PNAS USA* 81:6110–6114, 1984) and PII, two other gonococcal proteins, this information was used to construct a pair of oligonucleotides, designated as NC1 and NC2, shown in FIG. 2. NC1 is a unique sequence and NC2 is a mixed population of nucleotides intended to increase the probability of identifying the correct sequence. In colony hybridization assays, both these oligonucleotides hybridized to FA19, but did not hybridize to HB101 containing either pBR322 or pGEM-2.

Restriction endonuclease-digested DNA was run on agarose gels, and transferred from the gels to a nitro-cellulose filter by the blot technique of Southern (*J. Mol. Biol.* 98:503–517, 1978). The NC1 and NC2 oligo probes were labelled with $\gamma$-$P^{32}$-ATP (ICN Radiochemicals, Irvine, Calif.) using polynucleotide kinase according to the method of Maniatis et al. (supra). End-labelling was performed in the following buffer: Tris-HCl (pH 7.6), 10 mM $MgCl_2$, 5 mM DTT (dithiothreitol), 0.1 mM spermidine and 0.1 mM EDTA. Hybridization of labelled oligonucleotides to DNA on nitrocellulose filters was carried out overnight in 4×SSPE (0.18 M NaCl, 10 mM $NaH_2$ $PO_4$ [pH 7.4], 1 mM EDTA), 2×Denhardt's solution (1×=0.02% Bovine Serum Albumin, 0.02% Ficoll 0.02% polyvinyl pyrrolidine), 20 mM sodium pyro-phosphate, 0.2% sodium dodecyl sulfate and 50 µg/ml salmon sperm DNA, with $10^6$ cpm of labelled oligo per ml of hybridization. Filters were washed in 1×SSC (0.15 M NaCl, 0.015 M sodium citrate), 5 mM sodium pyrophosphate and 0.1% sodium dodecylsulfate. Hybridization and wash temperatures were 46° C. and 40° C. for NC1 and NC2 respectively. Filters were washed in 5×SSC, dried, and exposed to Kodak X-ray film. Hybridization to a single fragment occurred in each case; the relevant fragments were: EcoRI-10 kb; SalI-5.5 kb; Sau3A1-900 bp; and TaqI-750 bp. Identical results were observed with both NC1 and NC2.

Cloning of Fragments

When libraries of colonies of HB101 containing EcoRI-or SalI-digested DNA cloned into pBR322 were probed with the oligonucleotide NC1 by colony hybridization, no positive colonies were observed. This supported earlier observation that suggested that PI may be lethal to E. coli. The smaller fragments of FA19 DNA, i.e., Sau3AI and TaqI digests which hybridized with the oligonucleotides were presumed not to contain the entire PI gene, and were selected as candidates for cloning.

Essentially the same procedure was followed for each fragment. For the Sau3AI fragment total FA 19 DNA was digested to completion with Sau3AI. Plasmid pGEM-2 (obtained from Promega Biotec, Madison, Wis.) DNA was digested with BamHI, and ligated with the Sau3AI fragments. Ligation of DNA fragments was carried out with T4 DNA ligase (New England Biolabs, Beverley, Mass.) at 4° C. for 16 hours, in the following buffer: 50 mM Tris-HCl (pH 7.6) 10 mM $MgCL_2$, 5% (w/v) polyethylene glycol 8000, 1 mM ATP, 1 mM DTT. The recombinant plasmids are transformed into E. coli HB101 by the calcium chloride procedure of Mandel and Higa (J. Mol. Biol. 53: 154, 1970); briefly, the bacterial cells are suspended in an ice-cold, sterile solution of 50 mM $CaCl_2$ and 10 mM Tris Cl, pH 8, and then mixed with the plasmid DNA in ligation buffer.

About 2000 transformants were recovered; bacterial colonies were transferred onto nitrocellulose filters which were prepared by hybridization according to the method of Grunstein and Hogness (PNAS USA 82: 3961–3965, 1975), and hybridization with oligo NC1 was observed. A single colony actually hybridized with the oligonucleotide. Plasmid DNA was amplified, harvested, digested with Sau3AI, and probed with oligo NC1 by the Southern hybridization procedure already described. A single fragment of 900 bp hybridized with the oligonucleotide, the same size as the Sau3AI genomic fragment of FA19 identified by earlier Southern hybridization. This fragment was excised and electroeluted from an agarose gel, and religated into a BamHI-digested pGEM-2 plasmid to create the recombinant plasmid pUNC3 (FIG. 2).

Substantially the same procedures just described were performed with the 750 bp TaqI fragment of FA19 which hybridized with oligo NC1. The TaqI fragment, however, was ligated into the AccI digestion site of pGEM-2, resulting in the recombinant plasmid pUNC11 (FIG. 2).

SUBCLONING AND SEQUENCING OF FRAGMENTS

Before sequencing, the 750 bp TaqI fragment was further digested into smaller restriction fragments of less than 300 bp with the enzymes RsaI and MspI. The fragment ends were then repaired and ligated into the SmaI site of M13 mp18 RF DNA as described by Norrander et al. (Gene 26:101–106, 1983). The single stranded DNA produced by this cloning vector is then used as a template to be sequenced by the method of Sanger et al. (PNAS USA 74, 5463–5467, 1977).

Dideoxynucleotides may be prepared in accordance with the methods described in Sanger, supra, and the references included therein (BRL, Gaithersburg, Md.). Four separate wells are set up for each DNA sample, one for each of the dideoxynucleotides ddA, ddT, ddC, and ddG. To each well added 2 μl of template DNA, and 2 μl of primer mix consisting of 11 μl (22 ng) M13 17 base primer from BRL, 11 μl TM (100 mMTris+50 mM MgCl, pH 8.5) and 66 μl of $H_2O$ (for 10 clones). These are spun, covered with plastic wrap, and incubated at 56° C. for 50–60 minutes.

After incubation, 2 μl of the appropriate NTP mix is added to each well: each mix will contain 10–500 μM of the ddNTP, and 6.25 μM of each of the regular dNTP's. Following addition of the NTP mix, 2 μl of Klenow mix was added to each well; Klenow mix consisted of: 11 μl Klenow (diluted to 1 U/μl); 11 μl 0.1 M dithiothreitol, 4.4 μl $^{35}$S-dATP, and 61.6 μl $H_2O$. The mixture is spun, covered with plastic wrap, and incubated at 30° C. for 15 minutes. To each well is added 2 μl chase mix (0.25 mM of all four dNTP's), and spun, and incubated again at 30° C. for 15 minutes. 2 μl of formamide dye is then added to each well, and then they are incubated at 80° C. for 15 minutes, uncovered.

At this point, the mixtures are ready for loading onto gels, or can be wrapped and stored at –80° C. The gels employed in the procedure have the following composition:

| Extension Gel (80%) | |
|---|---|
| 40% acrylamide | 16 ml |
| Urea | 40 g |
| 10× TBE* | 8 ml |
| $H_2O$ | 24 ml |
| 10% APS (Ammonium persulfate) | 1 ml |
| TEMED (tetramethylethylene diamine) | 20 μl |

*Tris Borate electrophoresis buffer; 89 mMTris + 89 mM boric acid

Gels are run at 60 Watts constant power for 3–4 hours and then fixed in 10% acetic acid and 10% methanol for 15 minutes; they are then dried on paper and exposed to Kodak X-Ray film.

Figure 4:
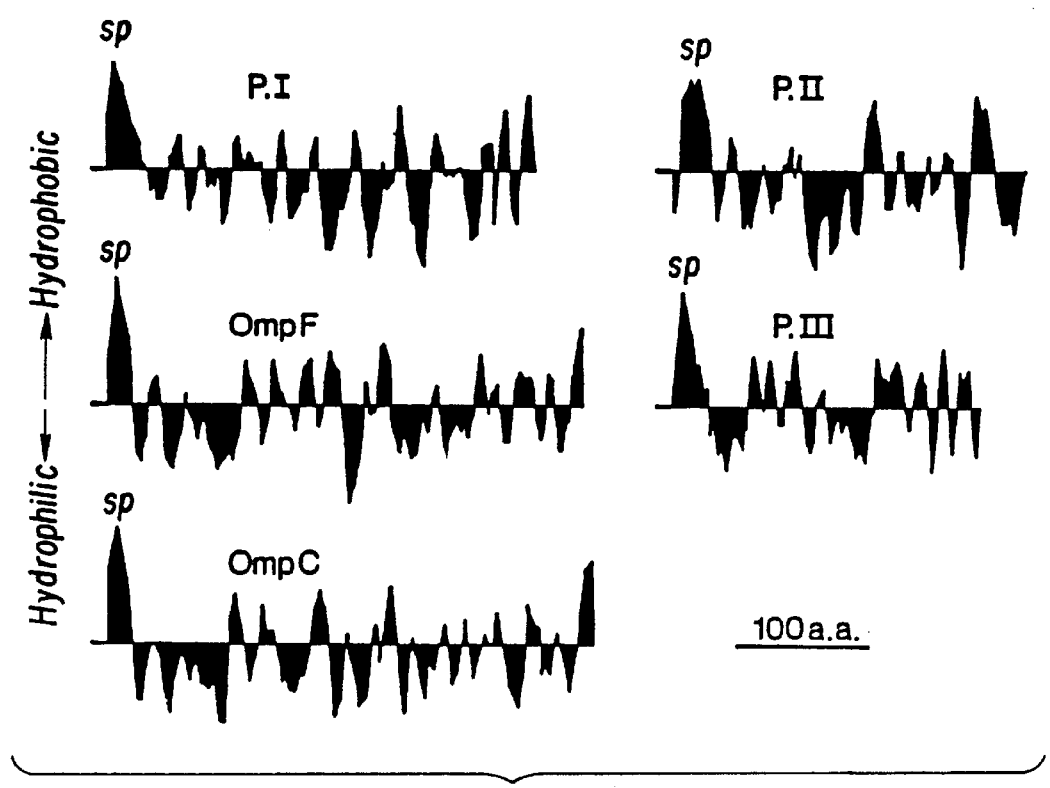
FIG. 4. Hydropathy patterns of the major outer membrane proteins of N. gonorrhoeae, PI, PII and PIII and the E. coli porins OmpF and OmpC; sp—signal peptide; a.a.—amino acid residues.

A new oligonucleotide, NC8 was created based on the sequence determined for the TaqI fragment. This new oligonucleotide, having the sequence 5' GCGTTAAAAC-CGCTACC 3' was used in a Southern hybridization to identify an 850 bp Sau 3 AI fragment adjacent to the 900 bp fragment previously cloned, and this 850 bp was cloned into pGEM-2, to give the plasmid pUNC15 (FIG. 2), and sequenced in the manner just described. The entire sequence of the PI gene is shown in FIG. 3. The only large open reading frame in this sequence lies between bases 84 and 1062, which corresponds to a protein of 326 amino acids. From the published N-terminal amino acid sequence of various PI proteins (Blake, supra), the first residue of the mature protein presumably was aspartic acid at base 141, giving a mature protein of 307 amino acids and a signal peptide of 19 amino acids. The predicted size of the protein was 33,786 daltons, which is close to the apparent molecular weight of 34,000 for PI in FA19. The signal peptide appeared to have the common characteristics associated with such sequences (Von Heijne, J. Mol. Biol. 184: 99–105, 1985), with a stretch of hydrophobic amino acids, an abundance of alanine residues and an Ala-X-Ala cleavage site. There were also putative –35 and –10 promoter sequences, which are close in sequence and separation to the consensus for these sequences in E. coli (Harley et al., Nucl. Acid Res. 15: 2343–2361, 1987), and a Shine-Dalgarno ribosomal binding site just upstream of the first residue of the signal sequence. The predicted N-terminal amino acid sequence matches that determined by amino acid sequencing of a putative PIA protein (Blake in The Pathogenic Neisseria, G. K. Schoolnik, ed., Amer. Soc. Microbiol., Wash.) and was very similar to that of the PIB protein of R10. The hydropathy profile of the predicted protein was typical of that of an outer membrane porin protein and compared favorably with major porins of E. coli, OmpF and OmpC (FIG. 4), characterized by long hydrophilic regions without any substantial hydrophobic stretches. There was little correlation with the hydropathy profiles of other sequenced gonococcal outer membrane proteins.

Gene Expression

Attempts to recover an intact PI gene clone by ligating the two portions of the gene of the Sau3AI fragments of pUNC3 and pUNC15 failed repeatedly, leading to the conclusion that gonococcal PI is lethal to E. coli. Therefore, a recombinant plasmid was constructed so that a portion of the PI gene promoter was removed and the PI gene was positioned downstream of the phage T7 promoter on pGEM-2. Since E. coli cells do not usually contain T7 polymerase, which transcribe genes downstream from T7 promoters, the plasmid is stably maintained.

Figure 5:
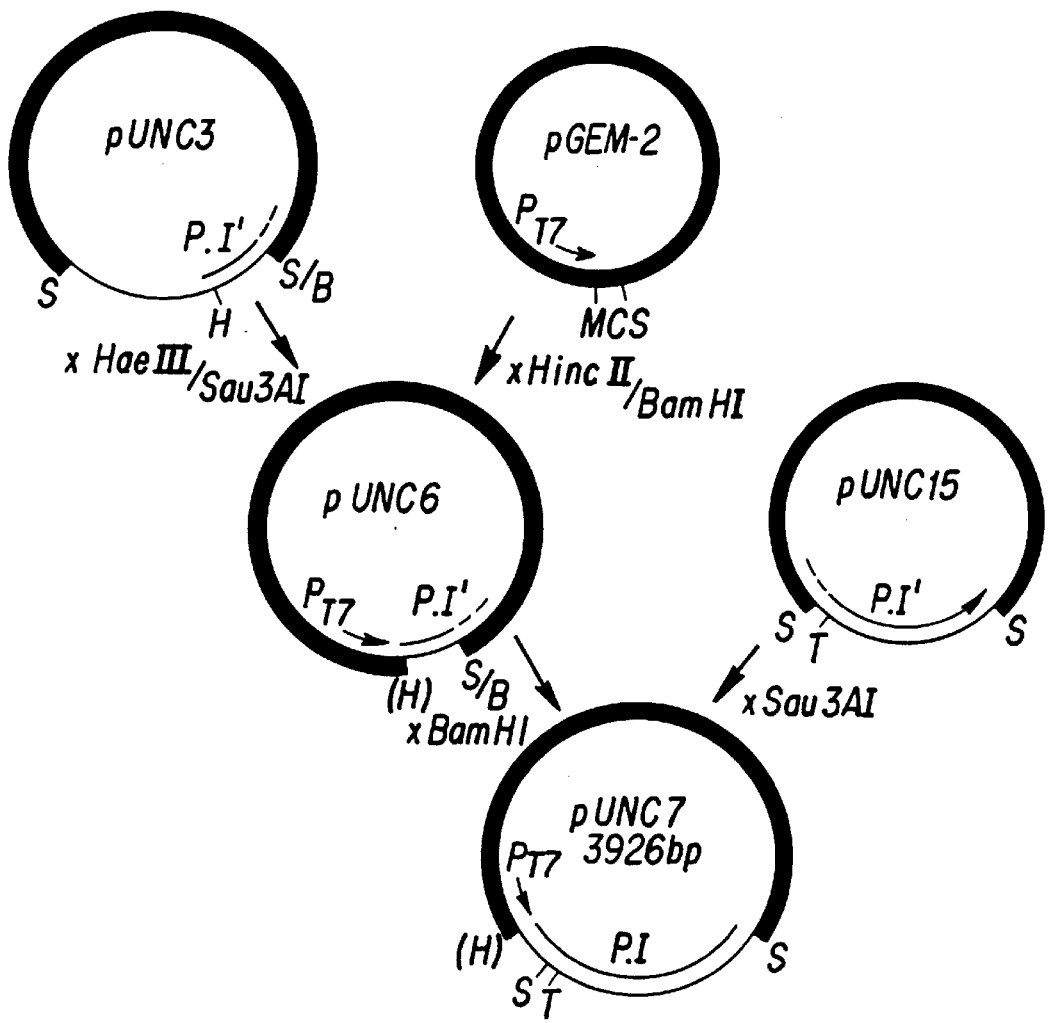
FIG. 5. Scheme of construction of pUNC7. A convenient HaeIII site between the −35 and −10 regions of the PI gene promoter allowed the removal of the −35 region and upstream sequence, followed by the reconstruction of the PI gene under the control of the phage T7 promoter on the vector plasmid pGEM-2. The thick line represents pGBM-2 DNA and the thin line FA19 DNA. PI'-portion of the PI gene (the dotted line indicates the direction of the missing segment of the gene); $P_{T7}$-phage T7 promoter; MCS-multiple cloning site; restriction enzyme sites: S-Sau3AI, H-HaeIII, B-BamHI, (H)-HaeIII/HincII junction (no site), T-TaqI.
Figure 6A:
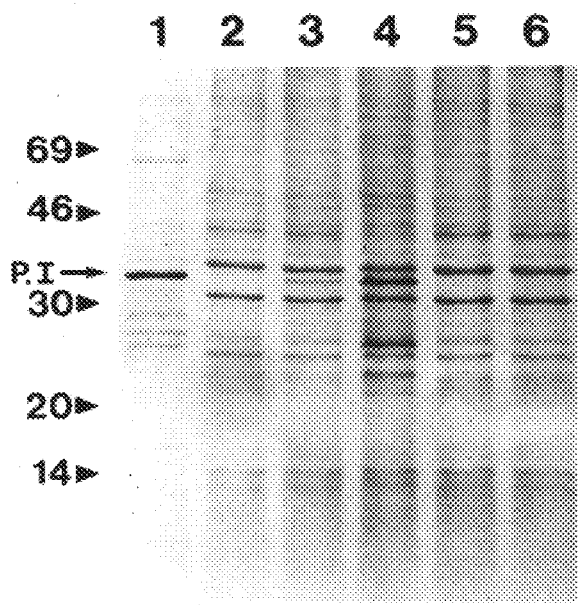
FIG. 6. Expression of the PI gene on pUNC7 in BL21 (DE3). A. NaDodSO$_4$-polyacrylamide gel electrophoresis of whole cell lysates on a 15% gel, stained with Coomassie blue. Marker protein sizes are shown to the left. PI is indicated, and the arrow in the center indicates a protein which is apparently missing in lane 4. B. Autoradiograph of a Western blot of the gel in A probed with the 6 PIA MAbs. Lanes are: 1. FA19; 2. BL21(DE3)pUNC7 grown 16 h without IPTG; 3. BL21(DE3)pUNC7 grown 3 H with IPTG; 4. BL21(DE3)pUNC7 grown 16 h with IPTG; 5. BL21 (DE3)pGEM-2 grown 16 h without IPTG; 6. BL21(DE3) pGEM-2 grown 16 h with IPTG.
Figure 6B:
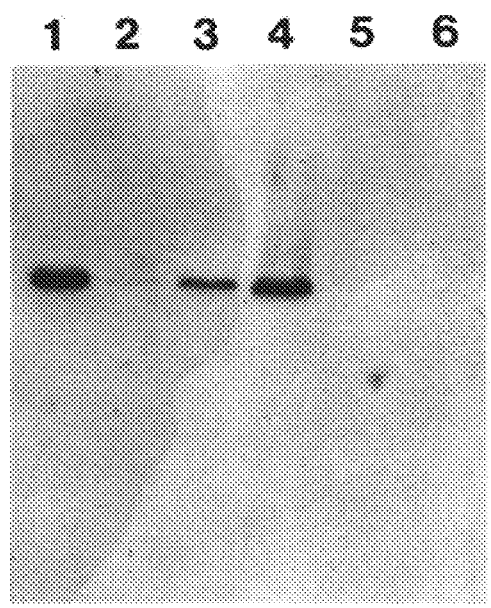

The plasmid so constructed is pUNC7, and was prepared in accordance with the scheme pictured in FIG. 5. A convenient HaeIII site between the −35 and −10 region of the PI gene promoter enabled an easy removal of the −35 region, and the sequence upstream. The remaining portion of the gene was then inserted into pGEM-2 under control of the T7 promoter. HB101 transformed with pUNC7 expressed no detectable PI in a colony radioimmmunoassay. Plasmid pUNC7 was then transformed into E. coli BL21 (DE3), a lysogen in which the phage T7 polymerase gene is present, but under control of the lac UV5 promoter (Studier et al., J. Mol. Biol. 189: 113–130, 1986). When grown on medium without isopropyl-β-D-thiogalactopyranoside (IPTG), BL21 (DE3) harboring plasmid pUNC7 produced no detectable PI, but when IPTG is present in the medium, inducing T7 polymerase production, the PI gene product was detected by PIA monoclonal antibodies in a colony blot radioixmunoassay The expressed protein is apparently efficiently exported through the inner membrane of the E. coli clone, since the product was detectable by colony radioimmunoassay without lysis of cells. The protein was of equivalent apparent molecular weight when compared with FA19 PI as detected by SDS-PAGE (FIG. 6A) and Western blotting (FIG. 6B), and is also apparently the most abundant protein produced by the clone during overnight growth in the presence of IPTG. Production of the protein was lethal to this particular E. coli strain, with no stable cells being recoverable. However, the plasmid pUNC7 containing the PI gene can be stably maintained in this strain, provided no expression is induced by growth on IPTG-containing medium. A biologically pure culture of strain BL21 (DE3) harboring plasmid pUNC7 has been deposited on Nov. 13, 1987 with the Northern Regional Research Laboratory (NRRL), under Accession No. NRRL #B-18263.

Example 2: Identification, Isolation, Sequencing and Expression of PIB Gene and Construction and Expression of PIA/B Hybrids The identification and isolation of both the PIB gene and PIA/B hybrids was the result of an attempt to show that the nmp locus is the PI structural gene, and that the PIA and PIB proteins are alleles. The sequence of events generally involved the insertion of a selectable marker into a PIA containing strain, followed by transformation of a PIB producing strain. These procedures are outlined in detail below.

Insertion of a Selectable Marker into the PI Gene

Figure 7:
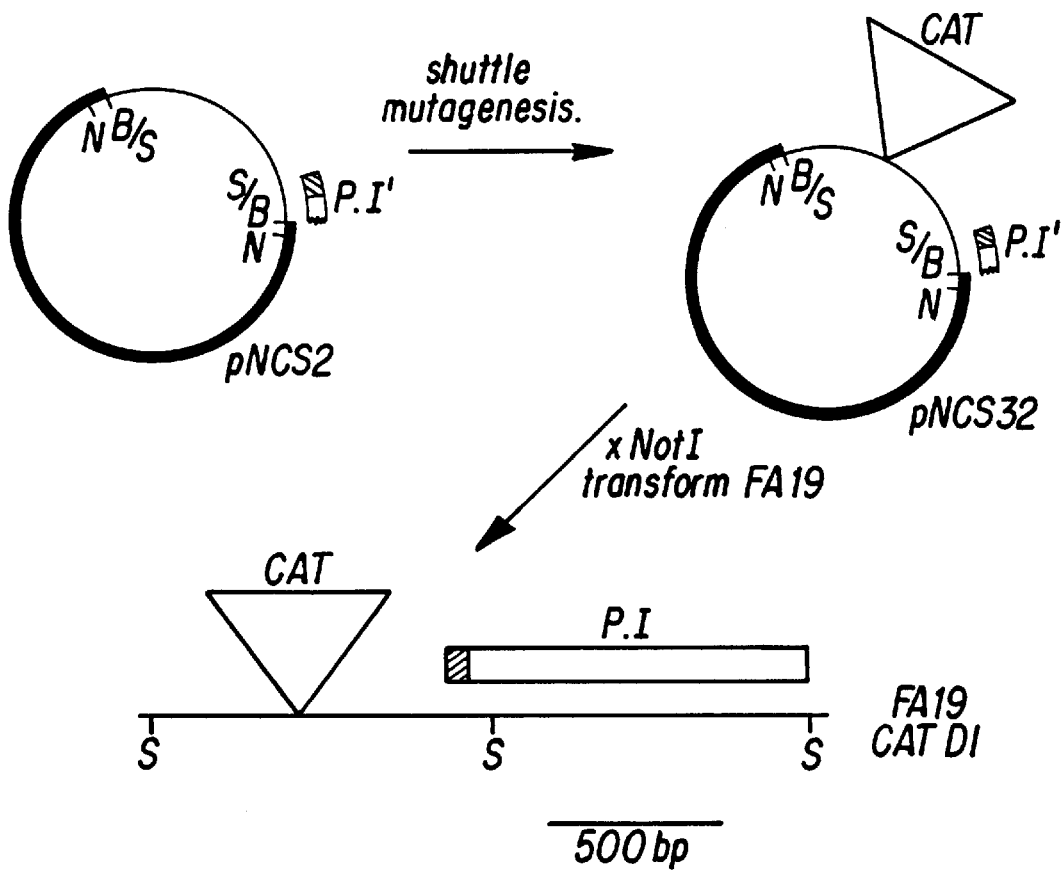
FIG. 7. Insertion of mTn3-CAT (C$\overset{A}{\underset{\vee}{T}}$CAT) adjacent to the PI structural gene of FA19. The thick line represents the vector pESS6 DNA. mTn3-CAT is 1.66 kb in length and is not drawn to scale. The position of the PI gene on the genome of FA19 CAT D1 is indicated by the bar above the line, the shaded box denoting the signal sequence. PI': portion of the PI gene present in the cloned constructs. Restriction enzyme sites: N-NotI; B-BamHI; S-Sau3AI.

The 900 bp Sau3AI fragment of pUNC3$_1$ described above, containing the first 45 codons of the PI gene of FA19 (a PIA producing strain), and upstream sequences, was ligated with BamHI-digested pHSS6 to form the plasmid pNCS2 (FIG. 7). This plasmid was then subjected to shuttle mutagenesis. Shuttle mutagenesis was performed using a modification of the method of Seifert et al., supra. The target DNA was subcloned into pHSS6 and introduced into E. coli strain RDP146 (pTCA) by transformation, followed by the introduction of pOX38::mTn3Cm-3 (from E. coli W3110polA) by conjugation. Transconjugants were grown overnight at 30° C. to allow transposition to occur, followed by several hour, growth at 37° C. A "pool" of transconjugants (approximately 1000 colonies) were resuspended and used as the donor in conjugation with E. coli NS2114Sm, in which plasmid cointegrates, formed as an intermediate in transposition events into the target plasmid, are resolved (Seifert et al., supra). The transposon thus inserted is stable since the transposase function, which is provided in trans on plasmid pTCA, is no longer present. The mini-transposon used in this case was mTn3Cm-3, in which the bla gene of Tn3 is replaced by the chloramphenicol acetyl transferase (CAT) gene.

After mapping the mTn3Cm-3 insertion sites within the 900 bp Sau3AI fragment of pNCS2, five such constructs with mTn3Cm-3 at various sites were digested with NotI, which releases the total insert as a linear fragment, and used to transform FA19. Only one digested plasmid, pNCS32 (FIG. 7), transformed FA19 to Cm$^r$, at a frequency of about $1 \times 10^{-7}$. The site of insertion of mTn3Cm-3 in pNCS32 was approximately 300 bp upstream of the PIA gene promoter sequences, while the insertion sites in the other four plasmids were all closer to, but not within, the PI gene. The location of mTn3Cm-3 in the genome of the transformant FA19 CAT D1 (FIG. 7) was confirmed by Southern hybridization.

Previous studies (Cannon et al., J. Bacteriol. 143:847–851, 1980; Infect. Immun. 32:547–552, 1981) have shown that the nmp locus, which affects the molecular weight and antigenicity of PI, is closely linked on the gonococcal genome to the antibiotic resistance markers str and spc, in the order str-spc-nmp, with cotransformation frequencies of 5% for str and nmp, and approximately 23% for spc and nmp. To determine whether the CAT marker in FA19 CAT D1, adjacent to the PI structural gene, showed the same linkage pattern as the nmp locus, reciprocal crosses were performed between the strains FA130 (Str$^r$ Spc$^r$ Cm$^s$; Sarubbi et al., J. Bacteriol. 120:1284–1292, 1974) and FA19 CAT D1 (Str$^s$ Spc$^s$ Cm$^r$). When FA130 DNA was used to transform FA19 CAT D1, selecting for either Str$^r$ or Spc$^r$, cotransformation frequencies were 26% (99/383) for spc and CAT and 7.5% (40/537) for str and CAT. In the reciprocal cross, selecting for Cm$^r$, the cotransformation frequencies were 10% (11/111) for spc and CAT and 1% (1/111) for str and CAT. Analysis of crossover classes confirmed that the gene order was str . . . spc . . . CAT. These data demonstrated that the CAT gene was linked to the str and spc markers in the same way as the nmp locus, providing strong evidence that the nmp locus is the structural gene for PI.

In another cross, FA19 CAT D1 DNA was used to transform the PIB strain MS11, selected for Cm$^r$. Among 45 transformants, 24 acquired the donor PIA, 13 retained the recipient PIB and 8 expressed novel hybrid PIA/PIB proteins, as detected by colony immunoblotting. The replacement of the recipient PIB by the PIA of the donor when selecting for the closely linked CAT gene confined the allelic nature of these genes, and the frequent occurrence of hybrid proteins suggested that the sequence homology between the two alleles allowed intragenic recombination to occur. Detailed analysis of these PI hybrid strains depended on knowledge of the PIB sequence of MS11, which was therefore cloned and sequenced.

Cloning, Sequencing and Expression of the PIB Gene

Figure 8:
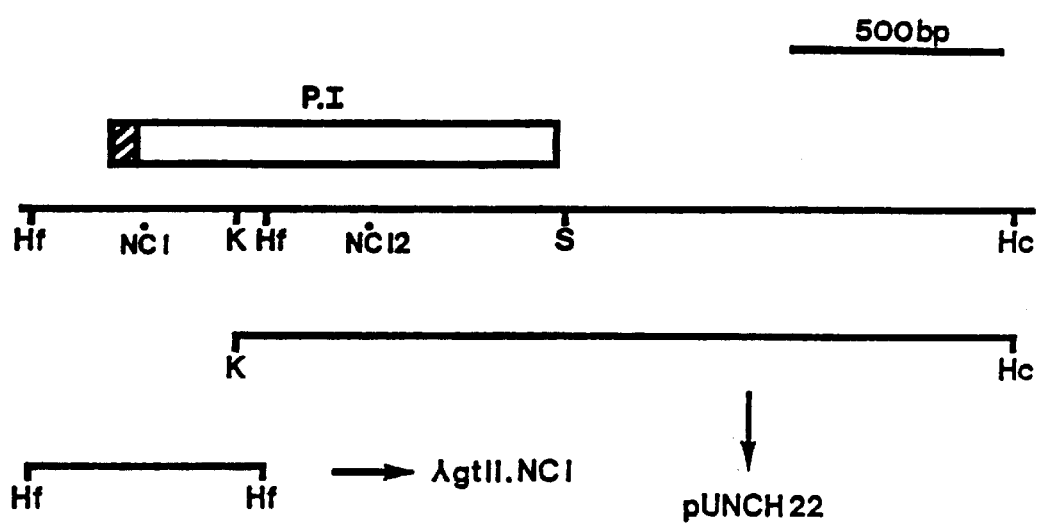
FIG. 8. Fragments of MS11 DNA cloned for the sequencing of the PI gene. The position of the PI gene is indicated by the bar above the line, the shaded box denoting the signal sequence. The location of the sequences of oligonucleotides NC1 and NC12 are shown. The larger fragment was cloned into the vector plasmid pGEM-3 and the smaller fragment into λgt11 to give constructs with the indicated designations. Restriction enzyme sites: Hf-HinfI; K-KpnI; S-Sau3AI; Hc-HincII.

Since intact gonococcal PI genes apparently cannot be cloned in E. coli, the strategy described above for PIA, of cloning fragments which together contain the complete gene sequence, was adopted for the MS11 gene. A DNA fragment from within the PI gene of the strain FA6149, previously characterized as having a hybrid PI (Danielson et al., Infect. Immun. 52:529–533, 1986), was cloned and sequenced, and revealed the presence of a KpnI site in the PIB portion of the sequence, approximately 300 bp from the start of the gene. Oligonucleotides NC12 (FIG. 8), derived from the PIB gene sequence downstream of the KpnI site, and NC1 (FIG. 1) derived from the gene sequence corresponding to the N-terminus of the protein, were used as probes in Southern hybridization to confirm the presence of the KpnI site in the MS11 PI gene. HB101 colonies containing KpnI/HincII-digested MS11 DNA cloned into the vector plasmid pGEm-3 were probed with these oligonucleotides, and colonies hybridizing with NC12 were detected and found to contain a plasmid with a 1.8 kb KpnI-HincII fragment which hybridized with NC12. This plasmid was designated pUNCH22 (FIG. 8). However, despite repeated attempts, no colonies hybridizing with NC1 were detected. Since NC1 hybridized with a 750 bp KpnI-HincII fragment of MS11 genomic DNA in Southern hybridization, the problem apparently was not one of size, but more likely the expression of the PI gene portion of this fragment which, in a high copy number vector, was lethal for HB101. For this reason the remaining portion of the MS11 PI gene was isolated as a 540 bp HinfI fragment in λgt11, using oligonucleotide NC1 as a probe. This clone was designated λgt11.NC1 (FIG. 8). The 540 bp HinfI fragment of λgt11.NC1 and the 750 bp KpnI-Sau3AI fragment of pUNCH22 were digested further, subcloned and sequenced. The sequence is shown in FIG. 9 and predicts a protein of 350 amino acids, of which the first 19 are the putative signal peptide. A comparison of the PI gene sequences of FA19 and MS11 reveals 80% nucleotide sequence homology. A comparison of the predicted amino acid sequences of PIA (FA19) and PIB (MS11) is presented in FIG. 10 and shows a number of regions of significant diversity interspersed with long regions of homology. Some of the regions of diversity presumably correspond to surface-exposed antigenic portions of the protein, since PI-specific monoclonal antibodies raised against whole gonococcal cells are never cross-reactive between PIA and PIB (Knapp et al., J. Infect. Dis. 150:44–48, 1984).

Figure 11:
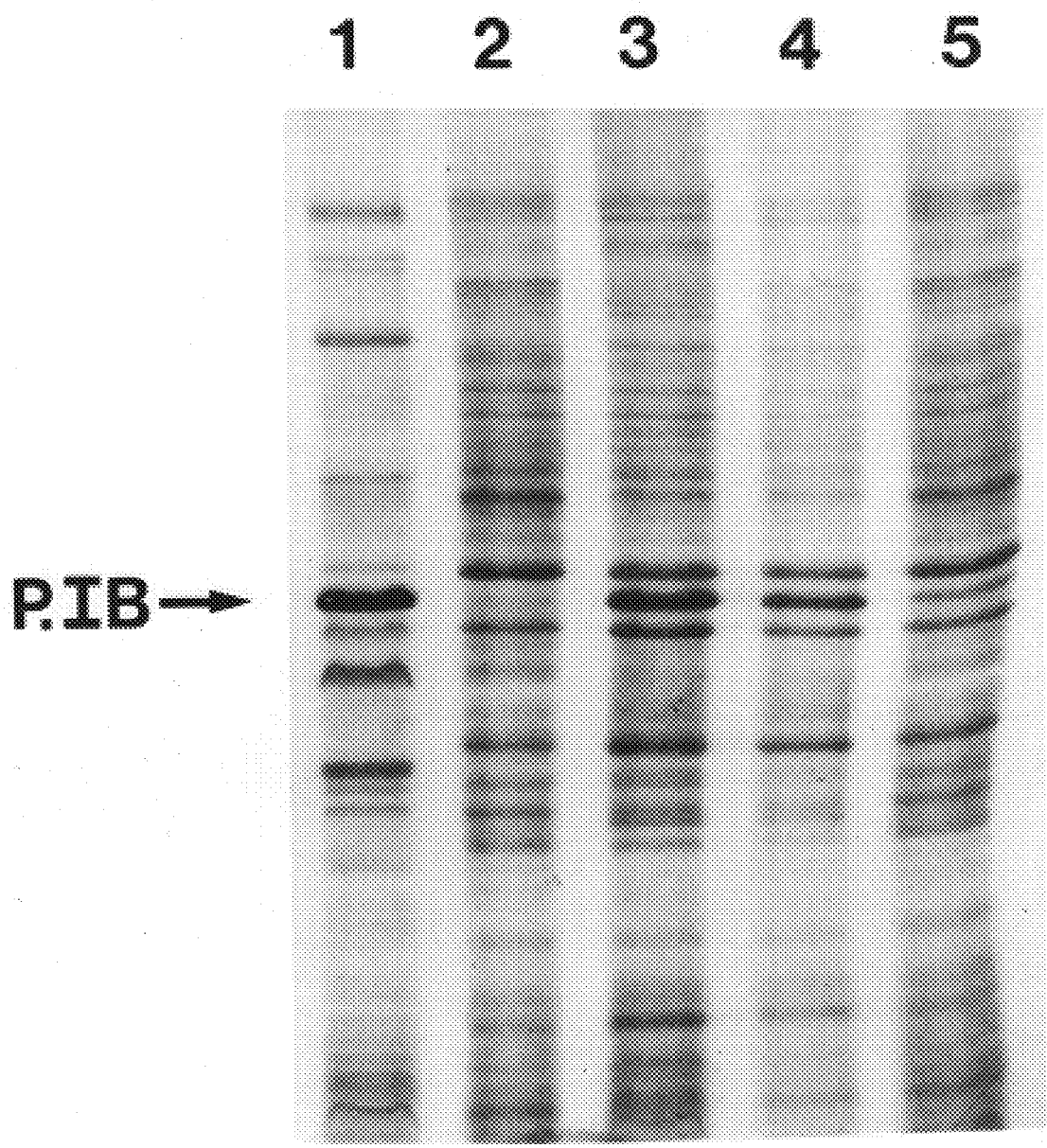
FIG. 11. Expression of the PIB gene on pUNCH25 in BL21(DE3) as detected by SDS-polyacrylamide gel electrophoresis of whole cell lysates on a 15% gel, stained with Coomassie blue. The PI protein band is indicated. Lanes are: 1. MS11; 2. BL21(DE3) pUNCH25 grown without IPTG; 3–5. BL21(DE3) pUNCH25 grown with IPTG. ITPG (50 µg/ml) was added to the growing culture at the following cell densities: 3. $5 \times 10^8$ cells/ml; 4. $10^9$ cells/ml; 5. $2 \times 10^9$ cells/ml. Expression of PI is greatest when the culture is induced earlier in the growth cycle.

Expression of a complete PIB gene was achieved using the same strategy as that for PIA (Section 6.2). A fragment of λgt11.NC1 insert DNA, from the NciI site between the −35 and −10 regions of the PIB gene promoter to the KpnI site within the gene, was ligated with the 750 bp KPnI-Sau3AI fragment of pUNCH22 into the vector pGEM-2 digested with HincII and BamHI. This resulted in a complete PIB coding sequence without its own promoter but immediately downstream of the T7 promoter on the plasmid vector. When this construct (pUNCH25) was introduced into BL21(DE3) and grown with IPTG, PIB expression was detectable (FIG. 11).

A biologically pure culture of E. coli strain BL21(DE3) harboring plasmid pUNCH25 has been deposited on Aug. 22, 1988 with the American Type Culture Collection, Rockville, Md., under Accession No. 67775.

Construction and Analysis of PIA/B Hybrid Strains

Further PIA/B hybrids were constructed by transforming (Biswas et al., J. Bacteriol. 129:983–992, 1977) MS11 with FA19 CAT D1 DNA, selecting $Cm^r$ and scoring PI by immunoblotting. In a reciprocal cross, DNA from $Cm^r$ transformant of MS11 that had retained its PIB was used to transform FA19, selecting for $Cm^r$ and scoring PI as before. Cells were incubated for phenotypic expression of antibiotic resistance for 5 hours either in GC base broth before plating or in GC base agar before addition of soft agar overlay containing the antibiotic. When using FA19 as recipient and selecting for $Cm^r$, 1 μg/ml of antibiotic was used, whereas when MS11 was recipient, 10 μg/ml was used. Bacterial strains were assayed for binding of monoclonal antibodies using a modification of the method of Cannon et al. A concentrated suspension of cells in GC base broth was transferred to nitrocellulose using a filtration manifold and lysed in chloroform vapor. The filter was soaked in TBS (10 mM Tris, pH 7.5, 150 mM NaCl) containing 5% dried milk, incubated in TBS containing the appropriate antibody, and then washed in TBS. After incubation in anti-mouse IgG-alkaline phosphatase conjugated secondary antibody (Sigma) and further washing, the filter was developed using nitroblue tetrazolium and 5-bromo-4-chloro-3-indolyl phosphate (Bethesda Research Laboratories) according to the manufacturer's directions. The monoclonal antibodies used were 4A12, 4G5, 2F12, 6D9, 5G9, 5D1 (10), 1D3 (26) and SM101 (27), all of which are PIA-specific, and 1F5, 3C8, 2D4 and 2H1 (10) which are PIB-specific. All antibodies except SM101 were kindly supplied in ascites by M. Tam (Genetic Systems), and were used at dilutions of 1:2000 to 1:10000. SM101 was kindly provided by J. Heckels (University of Southampton).

Figure 10:
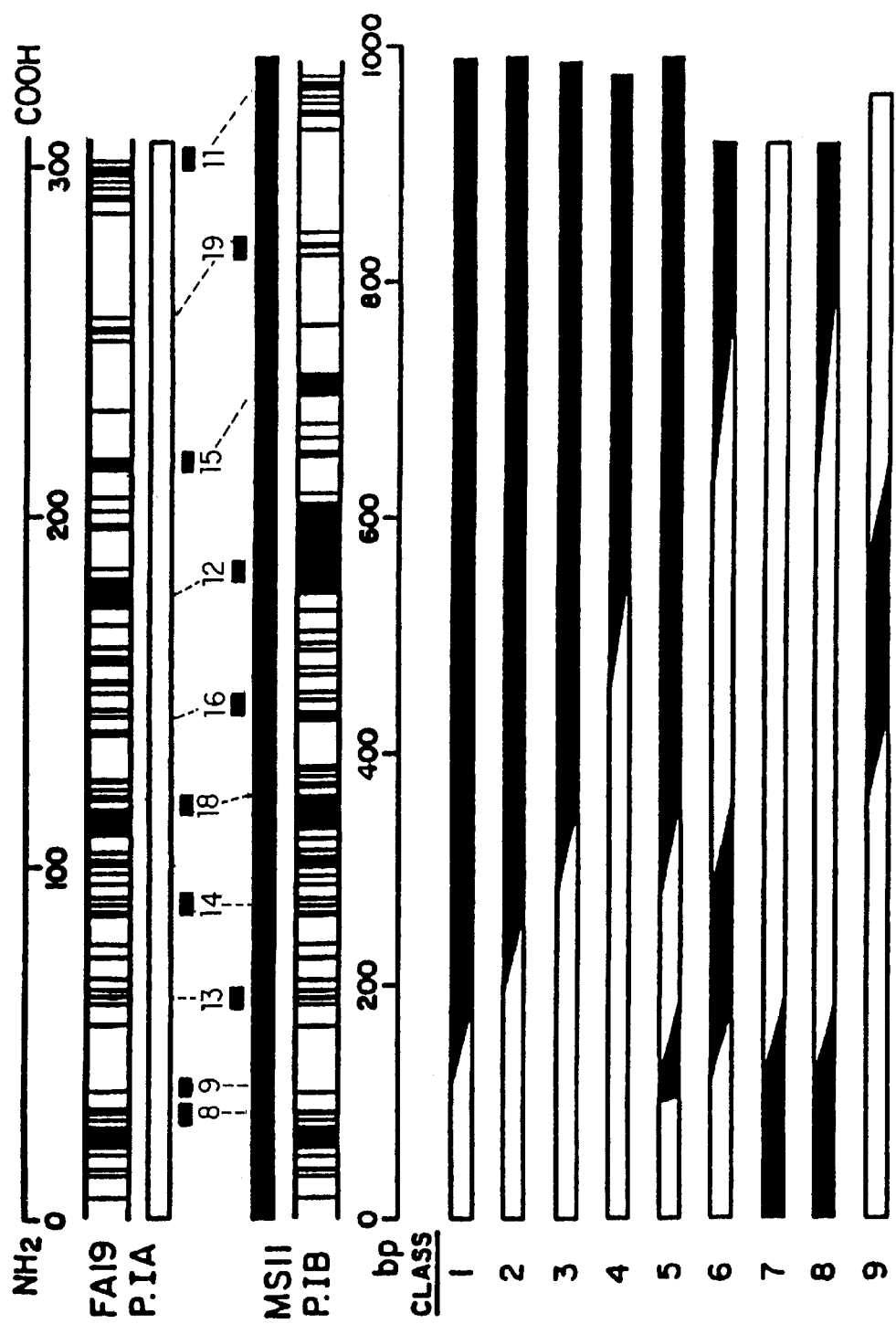
FIG. 10. Comparison of the amino acid sequences of FA19 PIA and MS11 PIB and structure of hybrid PI genes. PIA gene sequence is denoted by the open bar and PIB by the shaded bar. Above and below the PI genes are the comparisons of amino acid sequence, a vertical line corresponding to a single difference and a shaded block corresponding to a contiguous stretch of differences. The number of amino acid residues is shown on the scale above and the base pair numbers on the scale below. The oligonucleotides used to analyze the hybrids are shown between the genes, with the dotted line indicating the equivalent position on the other gene. The hybrid gene structures (classes 1–9) are shown below, and regions between oligonucleotide sequences where a crossover occurred are depicted by the slanted locations. The PI serovar of the different hybrid classes is shown in Table 1.

Among 300 transformants with FA19 as recipient, 3 had a hybrid PI. Among the 13 hybrid strains, 5 different hybrid PI serovars were identified (Table I). The hybrid strains were then analyzed by colony hybridization using a number of PIA- and PIB-specific oligonucleotides (Table II and FIG. 10), in order to assess which portions of the hybrid PI genes were PIA sequences and which were PIB sequences, and 9 different classes were detected by this method (FIG. 10). By analyzing the serovar of the hybrid PI genes of known structure, the approximate location of the epitopes for these monoclonal artibodies could then be determined.

TABLE I

Reactivities (Serovars) of Hybrid PI Strains with PI-Specific Monoclonal Antibodies

| Monoclonal Antibody | Hybrid Class (FIG. 10) | | | | | | |
|---|---|---|---|---|---|---|---|
| | 1–4 | 5 | 6 | 7–8 | 9 | FA19 | MS11 |
| 4G5 | + | + | + | − | + | + | − |
| 2F12 | + | + | + | − | + | + | − |
| SM101 | + | − | − | − | + | + | − |
| 6D9 | − | − | + | + | + | + | − |
| 4A12 | − | − | − | − | + | + | − |
| 5G9 | − | − | − | − | + | + | − |
| 5D1 | − | − | − | − | + | + | − |
| 1D3 | − | − | − | − | + | + | − |
| 1F5 | − | − | − | + | − | − | + |

TABLE I-continued

Reactivities (Serovars) of Hybrid PI Strains
with PI-Specific Monoclonal Antibodies

| Monoclonal | Hybrid Class (FIG. 10) | | | | | | |
|---|---|---|---|---|---|---|---|
| Antibody | 1–4 | 5 | 6 | 7–8 | 9 | FA19 | MS11 |
| 3C8 | + | + | − | − | + | − | + |
| 2D4 | + | + | − | − | − | − | + |
| 2H1 | + | + | − | − | − | − | + |

TABLE II

Oligonucleotides Used for Analysis of PI Hybrids

| Oligo-nucleo-tide | Sequence (5' -> 3') | PI Specificity | Location (Residue #s)* |
|---|---|---|---|
| NC8 | GCGTTAAAACCGCTACC | A | 27–32 |
| NC9 | TCGAACCCAAATCAGCG | A | 34–40 |
| NC11 | CGGTGTCGGTCTGCGCC | A | 299–305 |
| NC12 | GATACGGCGAAGGCACT | B | 182–187 |
| NC13 | CAAGGTGCCTCCGTCGC | B | 61–66 |
| NC14 | AAGTGCGCGTCGGCCGT | A | 87–92 |
| NC15 | GACTTGGCGCAACGATA | A | 213–219 |
| NC16 | GCAGCGTACAATACGCAC | B | 144–150 |
| NC18 | GCAACATTGCCCAACCC | A | 116–121 |
| NC19 | AGGCACTGTTGATAGTGC | B | 273–279 |

*The location refers to the amino acid residue numbers (where #1 is the first residue of the mature protein) encoded in whole or in part by the sequence of the oligonucleotide.

The epitopes for the PIA-specific monoclonal antibodies 4G5, 2F12 and SM101, which react with the class 1 hybrid, must be located near the N-terminus of the protein, within the first 60 residues. Comparison of hybrid classes 1, 5 and 6 suggests that the epitope for SM101 lies at least. partially in the region between residues 34 and 60. The N-terminal 60 residues contain significant diversity between PIA and PIB (FIGS. 3, 9, 10) which could account for the specificity of these antibodies. The epitope for 6D9 (PIA-specific), which reacts with hybrid classes 6–9, lies in the region of the protein between residues 187 and 250, which also includes regions of significant diversity between PIA and PIB. The epitopes for 4A12, 5G9, 5D1 and 1D3 (all PIA-specific) were detected only in the hybrid protein of class 9, and therefore presumably are complex epitopes involving both N-terminal and C-terminal portions of the protein. This is supported by the observation that these antibodies do not react well with PI in a Western blot, where the protein is relatively denatured.

Among the four antibodies that react with PIB of MS11, the epitope for 1F5, which reacts with hybrid classes 7 and 8, is located within the N-terminal 60 residues, while the epitopes for 3C8, 2D4 and 2H1 apparently lie within a central part of the protein, between residues 150 and 270, which includes a long stretch of divergent sequence. The epitope for 3C8 is located slightly upstream of those for 2D4 and 2H1, since the class 9 hybrid protein reacts with 3C8 only. However, these epitopes may be relatively complex since 2D4 and 2H1 do not reac with PIB in a Western blot. A biologically pure culture of the transformed microorganism FA6248, which contains a hybrid PIA/B gene and. expresses a hybrid PIA/B protein, has been deposited with the American Type Culture Collection, Rockville, Md., under Accession No. 53808.

Discussion

The present study, in which a reporter gene was inserted close to the PI structural gene, demonstrates that PIA and PIB structural genes are alleles of the same locus, which was previously identified as nmp (Cannon et al., *J. Bacteriol* 143:847–851, 1980). The presence of a single PI gene on the gonococcal genome is consistent with the observation that naturally-occurring strains possess either a PIA or a PIB protein, but never both, and that their PI serotype is stably maintained. A comparison of the PIA and PIB gene and deduced amino acid sequences revealed a high degree of homology, but regions of significant sequence divergence were identified. Although PI hybrids do not occur naturally, the PI hybrids that we constructed survived stably in vitro. However, the relatively infrequent formation of a hybrid PI with a PIB N-terminus and the surprisingly frequent occurrence of multiple crossovers within the PI gene suggests that certain classes of hybrid PI may be favored by gonococci growing in vitro.

The construction and analysis of PI hybrids allowed us to determine the approximate location of some of the surface-exposed portions of the proteins and provided some insight into their possible secondary and tertiary structures. The N-terminal regions of both PIA and PIB apparently are surface-exposed, along with at least one other region in the central part of each protein. The folding of PIA in the outer membrane may be such that N-terminal and C-terminal parts are closely associated on the surface, since epitopes for a number of PIA-specific monoclonal antibodies were identified only when both of these portions were present in a hybrid PI. These models for the conformation of PI in the outer membrane agree with some aspects of previous models based on proteolytic cleavage of PI in intact gonococci (Blake et al., *Infect. Immun.* 33:212–222, 1981; Judd et al. *Infect. Immun.* 54:408–414, 1986), but differ from previous suggestions that only the N-terminus of PIA and a central portion of PIB are surface-exposed (Blake et al., supra; Teerlink, *J. Exp. Med.* 166:63–76, 1987).

Deposit of Microorganisms

The following *E. coli* strains carrying the listed plasmids have been deposited with the Agricultural Research Culture Collection (NRRL), Peoria, IL or the American Type Culture Collection, (ATCC), Rockville, Md. and have been assigned the accession numbers indicated.

| *E. coli* Strain | Plasmid | Accession NO. |
|---|---|---|
| BL21 (DE3) | pUNC7 | NRRL B-18263 |
| BL21 (DE3) | pUNCH25 | ATCC 67775 |
| *N. gonorrhoeae* FA 6248 | | ATCC 53808 |

The present invention is not to be limited in scopes by the deposited strains, since each is intended as a single illustration of one aspect of the invention, and any cell lines which are functionally equivalent are within the scope of the invention. Indeed, various modifications of the invention in addition to those shown and described herein will become apparent to those skilled in the art from the foregoing description. Such modifications are intended to fall within the scope of the appended claims.

It is also to be understood that all base pair sizes given for nucleotides are approximate and are used for purposes of description.

What is claimed is:

1. A recombinant plasmid vector comprising a substantially purified nucleic acid molecule encoding all or a fragment of the amino acid sequence of Protein IB of *Neisseria gonorrhoeae* wherein said fragment is able to be bound by an antibody directed to Protein IB, the vector is stably maintained in a host cell, and the protein expression is controlled by an inducible promoter.

2. The recombinant plasmid vector of claim 1 wherein said amino acid sequence is depicted in FIG. 9.

3. The recombinant plasmid vector of claim 1 wherein the nucleic acid molecule is a substantially purified cDNA for protein IB of *Neisseria gonorrhoeae* having the nucleotide sequence as depicted in FIG. 9.

4. The recombinant plasmid vector of claim 1 wherein said vector is derived from plasmid pGEM-2.

5. The recombinant plasmid vector of claim 4 wherein the plasmid is pUNCH25.

6. A unicellular organism containing the vector of claim 1.

7. A unicellular organism containing the vector of claim 5.

8. The unicellular organism of claim 7 having all the identifiing characteristics of ATCC 67775.

9. A method for producing a PIB peptide of *Neisseria gonorrhoeae* having the amino acid sequence of Protein PIB or a fragment thereof said fragment being able to be bound by an antibody directed to Protein PIB, comprising:

(a) culturing in the absence of an inducer a host cell containing a replicable recombinant plasmid vector having a DNA sequence encoding the PIB peptide, which sequence is controlled by an inducible promoter and is stably maintained in a host cell; and (b) subsequently thereto, culturing the host cell in the presence of the inducer so that the PIB peptide is selectively expressed.

10. The method of claim 9 wherein the plasmid comprises the sequence as depicted in FIG. 9.

11. The method of claim 10 wherein the plasmid is derived from pGEM-2.

12. The method of claim 11 wherein the plasmid is pUNCH25.

* * * * *

UNITED STATES PATENT AND TRADEMARK OFFICE
CERTIFICATE OF CORRECTION

PATENT NO.   : 6,068,992
DATED        : May 30, 2000
INVENTOR(S)  : Carbonetti et al.

It is certified that error appears in the above-identified patent and that said Letters Patent is hereby corrected as shown below:

Column 1,
Line 27, now reads "cloned product of this particular DNA sequencie" should read -- cloned product of this particular DNA sequence --.

Column 3,
Line 42, now reads "rNA polymerase can recognize." should read -- RNA polymerase can recognize. --.

Column 4,
Line 63, now reads "napping as well as being" should read -- mapping as well as being --.

Column 8,
Line 19, now reads "Identification, Isolation and Sequence of the Pia" should read -- Identification, Isolation and Sequence of the PIA --.

Column 9,
Line 37, now reads "the PIA. gene, Verification of the" should read -- the PIA gene. Verification of the --.
Line 43, now reads "that each of these cligonucleotides" should read -- that each of these oligonucleotides --.

Column 10,
Line 13, now reads "in the Sanger method Up to" should read -- in the Sanger method. Up to --.

Column 12,
Line 52, now reads "to insert a selectable iaarker" should read -- to insert a selectable marker --.

UNITED STATES PATENT AND TRADEMARK OFFICE
CERTIFICATE OF CORRECTION

PATENT NO.   : 6,068,992
DATED        : May 30, 2000
INVENTOR(S)  : Carbonetti et al.

It is certified that error appears in the above-identified patent and that said Letters Patent is hereby corrected as shown below:

Column 19,
Lines 36-37, now reads "in a colony blot radioixmunoassay" should read -- in a colony blot radioixmunoassay. --.

Column 20,
Line 2, now reads "The 900 bp Sau3AI fragment of $pUNC3_1$" should read -- The 900 bp Sau3AI fragment of pUNC3, --.

Column 21,
Line 14, now reads "sequence, was adopted for the MS11 gene." should read
-- sequence, was adopted for the MS11 PI gene. --.

Column 24,
Line 3, now reads "since 2D4 and 2H1 do not reac with" should read -- since 2D4 and 2H1 do not react with --.
Lines 5-6, now reads "FA6248, which contains a hybrid PIA/B gene and. expresses" should read -- FA6248, which contains a hybrid PIA/B gene and expresses --.

Signed and Sealed this

Thirtieth Day of August, 2005

JON W. DUDAS
*Director of the United States Patent and Trademark Office*